United States Patent
Pudil et al.

(10) Patent No.: US 9,144,640 B2
(45) Date of Patent: Sep. 29, 2015

(54) SORBENT CARTRIDGE CONFIGURATIONS FOR IMPROVED DIALYSATE REGENERATION

(71) Applicants: Bryant J. Pudil, Plymouth, MN (US); Thomas E. Meyer, Stillwater, MN (US); David B. Lura, Maple Grove, MN (US); Martin T. Gerber, Maple Grove, MN (US)

(72) Inventors: Bryant J. Pudil, Plymouth, MN (US); Thomas E. Meyer, Stillwater, MN (US); David B. Lura, Maple Grove, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 418 days.

(21) Appl. No.: 13/836,973

(22) Filed: Mar. 15, 2013

(65) Prior Publication Data
US 2014/0217028 A1    Aug. 7, 2014

Related U.S. Application Data

(60) Provisional application No. 61/760,079, filed on Feb. 2, 2013.

(51) Int. Cl.
*A61M 1/16* (2006.01)

(52) U.S. Cl.
CPC ........... *A61M 1/1656* (2013.01); *A61M 1/1654* (2013.01); *A61M 1/1696* (2013.01)

(58) Field of Classification Search
CPC   A61M 1/1654; A61M 1/1656; A61M 1/1696
USPC ............................................... 210/195.2, 646
See application file for complete search history.

(56) References Cited

U.S. PATENT DOCUMENTS

| | | | |
|---|---|---|---|
| 3,608,729 | A | 9/1971 | Haselden |
| 3,669,880 | A | 6/1972 | Marantz et al. |
| 3,776,819 | A | 12/1973 | Williams |
| 3,884,808 | A | 5/1975 | Scott |
| 3,902,490 | A | 9/1975 | Jacobsen et al. |
| 4,209,392 | A | 6/1980 | Wallace |
| 4,376,707 | A | 3/1983 | Lehmann |
| 5,230,702 | A | 7/1993 | Lindsay et al. |

(Continued)

FOREIGN PATENT DOCUMENTS

| | | |
|---|---|---|
| EP | 266795 A2 | 5/1988 |
| EP | 0 614 081 B1 | 7/2000 |

(Continued)

OTHER PUBLICATIONS

U.S. Appl. No. 13/757,796, Medtronic, Inc.

(Continued)

*Primary Examiner* — Dirk Bass
(74) *Attorney, Agent, or Firm* — Hahn & Voight PLLC; Roger C. Hahn; Kenneth J. Collier

(57) ABSTRACT

A regeneration system that has a first regeneration module containing a first chosen regenerative substance; a second regeneration module containing the first chosen regenerative substance; and a first mixing chamber. A first outlet stream of a fluid sequentially exits the first mixing chamber, flows through the first regeneration module in fluid communication with the first chosen regenerative substance and returns to the first mixing chamber, and a second outlet stream of the fluid sequentially exits the first mixing chamber and flows through the second regeneration module in fluid communication with the first chosen regenerative substance.

52 Claims, 15 Drawing Sheets

(56) References Cited

U.S. PATENT DOCUMENTS

| | | |
|---|---|---|
| 5,284,470 A | 2/1994 | Beltz |
| 5,308,315 A | 5/1994 | Khuri et al. |
| 5,507,723 A | 4/1996 | Keshaviah |
| 5,662,806 A | 9/1997 | Keshaviah et al. |
| 5,849,179 A | 12/1998 | Emerson et al. |
| 5,858,186 A | 1/1999 | Glass |
| 5,944,684 A | 8/1999 | Roberts et al. |
| 6,114,176 A | 9/2000 | Edgson et al. |
| 6,126,831 A | 10/2000 | Goldau et al. |
| 6,521,184 B1 | 2/2003 | Edgson et al. |
| 6,627,164 B1 | 9/2003 | Wong |
| 6,666,840 B1 | 12/2003 | Falkvall et al. |
| 6,719,745 B1 | 4/2004 | Taylor |
| 6,814,724 B2 | 11/2004 | Taylor |
| 6,818,196 B2 | 11/2004 | Wong |
| 6,861,266 B1 | 3/2005 | Sternby |
| 6,878,283 B2 | 4/2005 | Thompson |
| 6,960,179 B2 | 11/2005 | Gura |
| 7,033,498 B2 | 4/2006 | Wong |
| 7,101,519 B2 | 9/2006 | Wong |
| 7,208,092 B2 | 4/2007 | Micheli |
| 7,241,272 B2 | 7/2007 | Karoor et al. |
| 7,276,042 B2 | 10/2007 | Polaschegg et al. |
| 7,326,576 B2 | 2/2008 | Womble et al. |
| 7,435,342 B2 | 10/2008 | Tsukamoto |
| 7,488,447 B2 | 2/2009 | Sternby |
| 7,537,688 B2 | 5/2009 | Tarumi et al. |
| 7,544,300 B2 | 6/2009 | Brugger et al. |
| 7,544,737 B2 | 6/2009 | Poss et al. |
| 7,563,240 B2 | 7/2009 | Gross et al. |
| 7,597,806 B2 | 10/2009 | Uchi et al. |
| 7,776,210 B2 | 8/2010 | Rosenbaum et al. |
| 7,794,419 B2 | 9/2010 | Paolini et al. |
| 7,850,635 B2 | 12/2010 | Polaschegg et al. |
| 7,922,686 B2 | 4/2011 | Childers et al. |
| 7,922,911 B2 | 4/2011 | Micheli |
| 7,947,179 B2 | 5/2011 | Rosenbaum et al. |
| 7,955,290 B2 | 6/2011 | Karoor et al. |
| 8,002,726 B2 | 8/2011 | Karoor et al. |
| 8,029,454 B2 | 10/2011 | Kelly et al. |
| 8,066,658 B2 | 11/2011 | Karoor et al. |
| 8,080,161 B2 | 12/2011 | Ding et al. |
| 8,087,303 B2 | 1/2012 | Beavis |
| 8,096,969 B2 | 1/2012 | Roberts et al. |
| 8,180,574 B2 | 5/2012 | Lo et al. |
| 8,187,250 B2 | 5/2012 | Roberts et al. |
| 8,197,439 B2 | 6/2012 | Wang et al. |
| 8,303,532 B2 | 11/2012 | Hamada et al. |
| 8,404,091 B2 | 3/2013 | Ding et al. |
| 8,409,444 B2 | 4/2013 | Wong |
| 2003/0080059 A1 | 5/2003 | Peterson et al. |
| 2003/0097086 A1 | 5/2003 | Gura |
| 2003/0105435 A1 | 6/2003 | Taylor |
| 2003/0114787 A1 | 6/2003 | Gura |
| 2004/0019312 A1 | 1/2004 | Childers et al. |
| 2005/0113796 A1 | 5/2005 | Taylor |
| 2005/0150832 A1 | 7/2005 | Tsukamoto |
| 2007/0007208 A1 | 1/2007 | Brugger et al. |
| 2007/0179431 A1 | 8/2007 | Roberts et al. |
| 2007/0213665 A1 | 9/2007 | Curtin et al. |
| 2008/0053905 A9 | 3/2008 | Brugger et al. |
| 2009/0020471 A1 | 1/2009 | Tsukamoto |
| 2010/0004588 A1 | 1/2010 | Yeh et al. |
| 2010/0084330 A1 | 4/2010 | Wong |
| 2010/0100027 A1 | 4/2010 | Schilthuizen et al. |
| 2010/0114012 A1 | 5/2010 | Sandford et al. |
| 2010/0217181 A1 | 8/2010 | Roberts et al. |
| 2010/0224492 A1 | 9/2010 | Ding et al. |
| 2011/0163034 A1 | 7/2011 | Castellarnau |

FOREIGN PATENT DOCUMENTS

| | | |
|---|---|---|
| EP | 711 182 B1 | 6/2003 |
| EP | 1592494 B1 | 6/2009 |
| EP | 1545652 B1 | 1/2013 |
| EP | 1345856 B1 | 3/2013 |
| EP | 2344220 B1 | 4/2013 |
| EP | 2575827 A2 | 4/2013 |
| EP | 2576453 A2 | 4/2013 |
| WO | WO 9532010 A1 | 11/1995 |
| WO | WO0185295 A2 | 11/2001 |
| WO | WO2004062710 A3 | 10/2004 |
| WO | WO2007089855 A2 | 8/2007 |
| WO | WO2009157877 A1 | 12/2009 |
| WO | WO2009157878 A1 | 12/2009 |
| WO | WO 2010/028860 A1 | 3/2010 |
| WO | WO2010102190 A4 | 11/2010 |
| WO | WO 2013019179 A1 | 2/2013 |
| WO | WO 2013019994 A3 | 4/2013 |
| WO | WO 2013025844 A3 | 5/2013 |
| WO | WO 2013028809 A3 | 5/2013 |

OTHER PUBLICATIONS

U.S. Appl. No. 13/836,973, Medtronic, Inc.
U.S. Appl. No. 13/835,735, Medtronic, Inc.
U.S. Appl. No. 13/836,079, Medtronic, Inc.
U.S. Appl. No. 13/791,755, Medtronic, Inc.
U.S. Appl. No. 13/586,824, Medtronic, Inc.
U.S. Appl. No. 13/612,701, Medtronic, Inc.

SORBENT CARTRIDGE CONFIGURATIONS FOR IMPROVED DIALYSATE REGENERATION

CROSS-REFERENCE

This application claims the priority of U.S. Provisional Application No. 61/760,079 filed on Feb. 2, 2013, the entire content thereof is incorporated herein by reference.

FIELD OF THE INVENTION

The invention relates to systems and methods for sorbent cartridge configurations that improve dialysate regeneration capacity and efficiency during hemodialysis, hemodiafiltration, peritoneal dialysis and hemofiltration.

BACKGROUND

Regenerative dialysis systems, such as the Recirculating Dialysate System ("REDY" System) contain regenerative substances that remove impurities, waste products and certain electrolytes from spent dialysate to result in cleansed dialysate that can be reconstituted and reused. Depending on the dialysis treatment being performed, several kilograms of sorbent materials may be required for dialysate regeneration. Hence, there is a need for systems and methods that minimize the amount of sorbent material required during hemodialysis, hemofiltration, hemodiafiltration and peritoneal dialysis. There is also a need for systems and methods having decreased weight and cost of a regeneration module. There is further a need for configurations of regeneration modules such as sorbent cartridges that reduce the amount of regenerative substances that are consumed during dialysate regeneration.

SUMMARY OF THE INVENTION

The invention is directed toward hemodialysis, hemofiltration, hemodiafiltration, and peritoneal dialysis systems having a dialysate regeneration system based on regenerative substances such as sorbent materials. In any embodiment, a regeneration system can have a first regeneration module containing a first chosen regenerative substance, a second regeneration module containing the first chosen regenerative substance, and a first mixing chamber wherein a first outlet stream of a fluid can sequentially exit the first mixing chamber flows through the first regeneration module in fluid communication with the first chosen regenerative substance and returns to the first mixing chamber, and a second outlet stream of the fluid can sequentially exit the first mixing chamber and flows through the second regeneration module in fluid communication with the first chosen regenerative substance.

In any embodiment, the regeneration system can have a first inlet stream of the fluid that enters the first mixing chamber and is mixed in the first mixing chamber with a second inlet stream of the fluid that enters the first mixing chamber. The regeneration system can also have a mixing chamber that has a static mixer element or a semi-permeable membrane that separates the first inlet stream from the second inlet stream, and a solute diffuses from the first inlet stream to the second inlet stream. In any embodiment, the second inlet stream consists of the first outlet stream returning to the first mixing chamber. In any embodiment, the first outlet stream and the second outlet stream can have substantially the same component concentrations. In any embodiment, the first regeneration module can operate at a total capacity of the first chosen regenerative substance. In any embodiment, the fluid can be a dialysate solution, and the first chosen regenerative substance can remove a waste species from the dialysate solution. In any embodiment, the fluid may be a filtrate solution, and the first chosen regenerative substance can remove a waste species from the filtrate solution.

In any embodiment, the first chosen regenerative substance can have at least one of urease, alumina, zirconium phosphate, zirconium oxide, activated carbon or other ion-exchange materials In any embodiment, the second regeneration module can have a second chosen regenerative substance wherein the first chosen regenerative substance removes a first waste species from the fluid, and the second chosen regenerative substance removes a second waste species from the fluid.

In any embodiment, the first chosen regenerative substance can have at least one of urease, alumina, zirconium phosphate, zirconium oxide, activated carbon, or other ion-exchange materials, and the second chosen regenerative substance comprises at least one of urease, alumina, zirconium phosphate, zirconium oxide, activated carbon, or other ion-exchange materials.

In any embodiment, the first chosen regenerative substance can have at least one of urease, alumina, zirconium oxide, or activated carbon, the second chosen regenerative substance comprises zirconium phosphate, and the first regeneration module and the second regeneration module each contain an equal quantity of the first chosen regenerative substance.

In any embodiment, a third regeneration module can have the first chosen regenerative substance; and a second mixing chamber, wherein a third outlet stream of the fluid exits the second mixing chamber and flows through the first mixing chamber, a fourth outlet stream of the fluid exits the second mixing chamber and flows through the third regeneration module, a third inlet stream of the fluid enters the second mixing chamber, the fourth inlet stream enters the second mixing chamber, the first inlet stream consists of the third outlet stream, and the fourth inlet stream consists of the second outlet stream.

In any embodiment, a first pump can operate to cause the fluid to flow through the first mixing chamber.

In any embodiment, a second pump between the first mixing chamber and the second regeneration module can operate to cause the second outlet stream to flow.

The present regeneration system can have a regeneration module containing a regenerative substance; and a counter-current sorbent cartridge containing a regenerative substance, wherein a first stream of a fluid enters the counter-current sorbent cartridge in fluid communication with the regenerative substance, a second stream of the fluid exits and reenters the counter-current sorbent cartridge, and a third stream of the fluid exits the counter-current sorbent cartridge and flows through a second regeneration module in fluid communication with a regenerative substance.

In any embodiment, the regeneration system can further include a microbial filter positioned downstream of the first mixing chamber along a fluid flow.

In any embodiment, the regeneration system can further include a replacement fluid pump upstream of the microbial filter along the fluid flow.

In any embodiment, the regeneration system can further include a first pump positioned upstream of the first regeneration module and a second pump positioned upstream of the second regeneration module.

In any embodiment, at least one of the first and second regeneration modules of the regeneration system can include first and second compartments, the first and second compartments being separated with a barrier oriented in a direction substantially parallel to a fluid flow.

In any embodiment, the first and second compartments can be different in composition.

The present regeneration system can have a regeneration module containing a first chosen regenerative substance, a second chosen regenerative substance and a mixing chamber contained in a single housing unit. The first and second regenerative substances can have at least one of urease, alumina, zirconium phosphate, zirconium oxide, activated carbon, or other ion-exchange materials.

In any embodiment, the first stream can be mixed in the mixing chamber with the second stream reentering the mixing chamber.

In any embodiment, the second stream and the third stream exiting the mixing chamber can have substantially the same component concentrations.

In any embodiment, the fluid can have a dialysate solution, and the regenerative substance removes a waste species from the dialysate solution.

In any embodiment, the fluid can have a filtrate solution, and the regenerative substance can remove a waste species from the filtrate solution.

In any embodiment, the regenerative substance can have at least one of urease, alumina, zirconium phosphate, zirconium oxide, activated carbon, or other ion-exchange materials.

In any embodiment, a dialysis system can have a dialyzer that facilitates transfer of a solute from blood to a dialysate; a first regeneration module having a first chosen regenerative substance; a second regeneration module containing the first chosen regenerative substance; and a first mixing chamber, wherein a first outlet stream of the dialysate can sequentially exit the first mixing chamber, flows through the first regeneration module in fluid communication with the regenerative substance and returns to the first mixing chamber, and a second outlet stream of the dialysate can sequentially exit the first mixing chamber, flow through the second regeneration module in fluid communication with the regenerative substance and flows through the dialyzer.

The present invention relates to a filtration system that can have a filter that facilitates removal of a filtrate from blood; a first regeneration module containing a first chosen regenerative substance; a second regeneration module containing the first chosen regenerative substance; and a first mixing chamber, wherein a first outlet stream of the filtrate can sequentially exit the first mixing chamber, flows through the first regeneration module in fluid communication with the regenerative substance and returns to the first mixing chamber, and a second outlet stream of the filtrate can sequentially exit the first mixing chamber, flows through the second regeneration module in fluid communication with the regenerative substance and flows through the dialyzer.

The present invention also relates to a method of regenerating a fluid that can have the steps of conveying a first outlet stream of the fluid from a first mixing chamber to a first regeneration module containing a first chosen regenerative substance; removing a waste species from the first outlet stream in fluid communication with the regenerative substance; returning the first outlet stream to the first mixing chamber; mixing a first inlet stream of the fluid entering the first mixing chamber with the first outlet stream returned to the first mixing chamber; conveying a second outlet stream of the fluid from the first mixing chamber to a second regeneration module containing the first chosen regenerative substance; and removing the waste species from the second outlet stream in fluid communication with the regenerative substance.

DETAILED DESCRIPTION

Definitions

Figure 1:
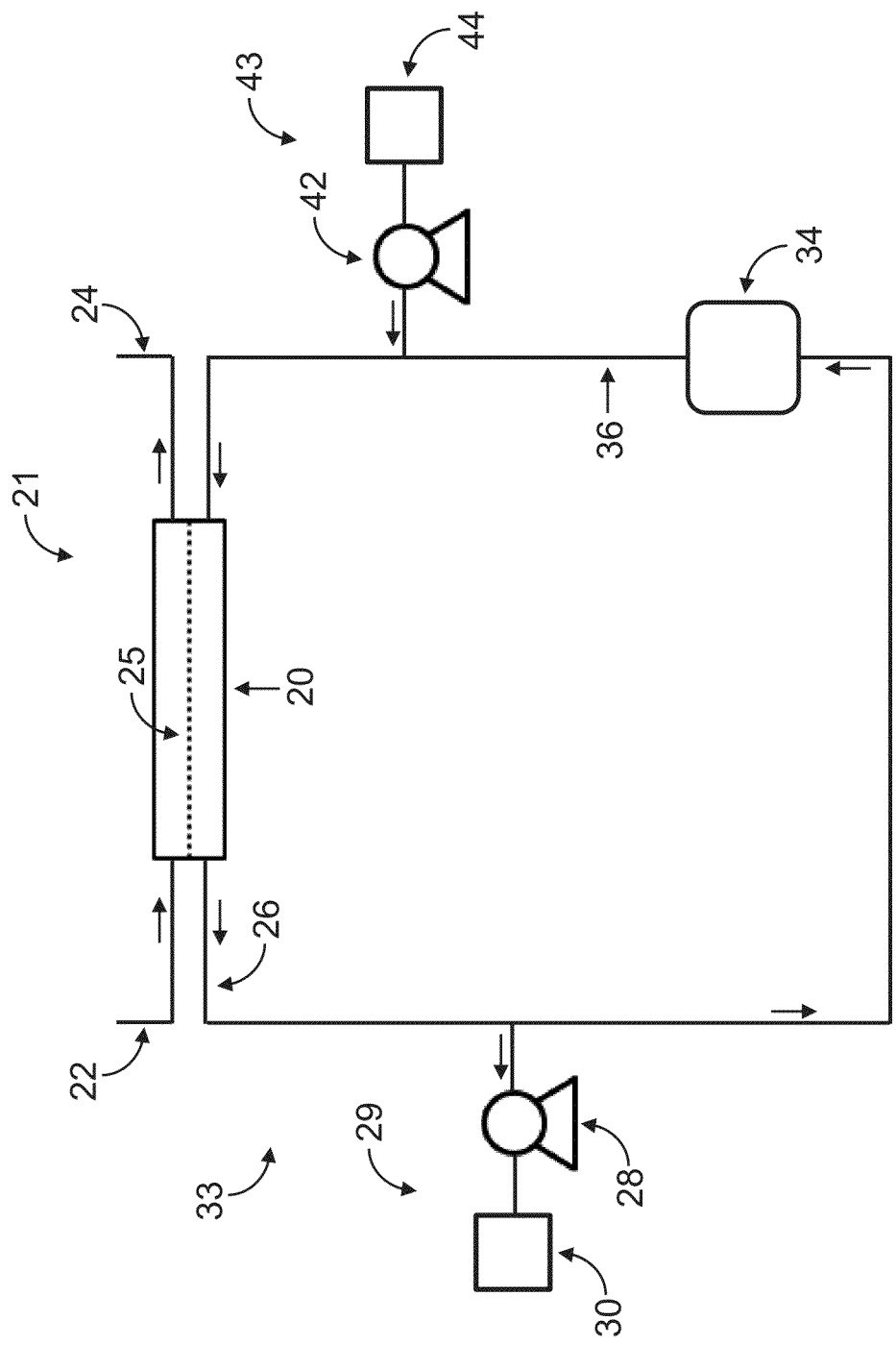
FIG. 1 is a flow diagram of a dialysate regeneration system associated with a controlled compliant dialysate circuit.

Unless defined otherwise, all technical and scientific terms used herein generally have the same meaning as commonly understood by one of ordinary skill in the relevant art. The definitions provided herein should not be rigidly construed without taking into account the context and other ascribed meanings provided, or by their use, in other parts of the specification, claims, and drawings.

The articles "a" and "an" are used herein to refer to one or to more than one (i.e., to at least one) of the grammatical object of the article. By way of example, "an element" means one element or more than one element.

The term "substantially" refers to an extent of similarity between any two given values that is at least 75 percent, 80 percent, 85 percent, 90 percent, 95 percent, or 99.9 percent, the given values optionally including values in weight, height, length, area, temperature, angle dimensions, among others.

The term "total capacity" refers to a characteristic of a regenerative substance, wherein when the chosen regenerative substance has reached "total capacity" it can no longer remove certain species from a solution passing through the chosen regenerative substance. The term "total capacity"

refers to the total amount of a certain species that can be removed from a solution in contact with a chosen regenerative substance.

The term "acid or base equivalents" refers to an equivalent acid or base donating or accepting an equal number of moles of hydrogen or hydronium ions per mole of the acid to which the equivalent acid is being equated, or mole of hydroxide ions to which the equivalent base is being equated.

The term "cation infusate pump" historically known as an "acid concentrate pump" in dialysis systems refers to a pump that serves the function to move or control the flow of a fluid to and/or from a reservoir having a substance that contains at least one cation species, such as calcium, magnesium and potassium ions. In the present invention, the historically used term of "acid concentrate pump" is used.

The term "acid feed" refers a state of fluid communication that enables an acid solution to be obtained from an acid source and connected or feed into a receiving source or flow path.

An "acid" can be either an Arrhenius acid, a Brønsted-Lowry acid, or a Lewis acid. The Arrhenius acids are substances or fluids which increase the concentration of hydronium ions (H3O+) in solution. The Brønsted-Lowry acid is a substance which can act as a proton donor. Lewis acids are electron-pair acceptors.

The term "activated carbon" may refer to a porous carbon material having a surface area greater than 500 m² per gram. Activated carbon can be capable of absorbing several species including heavy metals such as lead, mercury, arsenic, cadmium, chromium and thallium among others, oxidants such as chlorine and chloramines, fluoride ions, and waste species such as phosphate and certain nitrogen-containing waste species such as creatinine and uric acid.

The terms "administering," "administer," "delivering," "deliver," "introducing," and "introduce" can be used, in context, interchangeably to indicate the introduction of water or a dialysate having an altered concentration of at least one component, including electrolytes and alkali and/or alkali earth ions, to a patient in need thereof, and can further mean the introduction of water, any agent or alkali and/or alkali earth ions to a dialysate or dialysis circuit where such water, agent or alkali and/or alkali earth ion will enter the blood of the patient by diffusion, transversal of a diffusion membrane or other means.

The term "air trap" refers to a structure for separating a gas from a mixture of a gas and a liquid or any other separation means known in the art. An air trap can include a hydrophobic membrane for allowing gases to pass and for preventing the passage of water.

The term "albumin sieving coefficient" can be used to describe the amount of albumin that will cross a membrane.

The terms "ammonia sensing module" and "ammonia detector" refer to a unit that performs all or part of the function to detect a predetermined level of, or measure a concentration of, ammonia and/or ammonium ions in a fluid.

The term "anion exchange membrane" refers to a positively charged membrane, which allows negatively charged ions (anions) to pass through.

The term "anticoagulant" is a substance that prevents or delays the clotting of blood, such as heparin, Fragmin®, and sodium citrate.

The term "atmospheric pressure" refers to the local pressure of air in the environment in proximity to the system at the time that the system is operating.

The term "base concentrate pump" refers to a device that performs work on a fluid solution to cause fluid flow to control the volume transfer of a basic or alkaline solution into a circuit.

The term "base concentrate reservoir" refers to a vessel or container, optionally accessible by a pump that contains a variable amount of a basic or alkaline fluid solution.

The term "base module" refers to a basic unit of an apparatus for hemodialysis, hemodiafiltration, or hemofiltration that incorporates one or more fluid pathways. Exemplary, non-limiting components that can be included in the base module include conduits, valves, pumps, fluid connection ports, sensing devices, a controller and a user interface. The base module can be configured to interface with reusable or disposable modules of the apparatus for hemodialysis, hemodiafiltration, or hemofiltration to form at least one complete fluid circuit, such as a dialysis, cleaning, disinfection, priming or blood rinse back circuit.

A "base" can be either a substance that can accept hydrogen cations (protons) or more generally, donate a pair of valence electrons. A soluble base is referred to as an alkali if it contains and releases hydroxide ions (OH⁻) quantitatively. The Brønsted-Lowry theory defines bases as proton (hydrogen ion) acceptors, while the more general Lewis theory defines bases as electron pair donors, allowing other Lewis acids than protons to be included. The Arrhenius bases act as hydroxide anions, which is strictly applicable only to alkali.

The term "base feed" refers a state of fluid communication that enables a base solution to be obtained from a base source and connected or feed into a receiving source or flow path.

The term "bicarbonate buffer component" refers to any composition contain bicarbonate (HCO₃⁻) ion or a conjugate acid of bicarbonate ion in any amount, proportion or pH of the composition. The bicarbonate buffering system is an important buffer system in the acid-base homeostasis of living things, including humans. As a buffer, it tends to maintain a relatively constant plasma pH and counteract any force that would alter it. In this system, carbon dioxide (CO₂) combines with water to form carbonic acid (H₂CO₃), which in turn rapidly dissociates to form hydrogen ions and bicarbonate (HCO₃⁻) as shown in the reactions below. The carbon dioxide-carbonic acid equilibrium is catalyzed by the enzyme carbonic anhydrase; the carbonic acid-bicarbonate equilibrium is simple proton dissociation/association and needs no catalyst.

$$CO_2 + H_2O \leftrightarrows H_2CO_3 \leftrightarrows HCO_3^- + H^+$$

Any disturbance of the system will be compensated by a shift in the chemical equilibrium according to Le Chatelier's principle. For example, if one attempted to acidify the blood by dumping in an excess of hydrogen ions (acidemia), some of those hydrogen ions will associate with bicarbonate, forming carbonic acid, resulting in a smaller net increase of acidity than otherwise.

The term "bicarbonate buffer concentrate" refers to a bicarbonate (HCO₃⁻) buffer component composition at a higher concentration than found at normal physiological levels that can be used to for instants to readjusted the pH of the dialysate (see also definition of bicarbonate buffer component relating to its use).

The term "bicarbonate cartridge" refers to a container that can be a stand-alone container or alternatively can be integrally formed with an apparatus for hemodialysis, hemodiafiltration, or hemofiltration. The bicarbonate cartridge can store a source of buffering material, such as sodium bicarbonate, and can be configured to interface with at least one other functional module found in systems for hemodialysis, hemodiafiltration, or hemofiltration. For example, the bicarbonate cartridge can contain at least one fluid pathway and include components such as conduits, valves, filters or fluid connection ports. The bicarbonate cartridge can be disposable or be consumable wherein the cartridge is recharged upon depletion. Specifically, the term "bicarbonate consumables container" refers to an object or apparatus having or holding a material in solid and/or solution form that is a source of bicarbonate, such as sodium bicarbonate, that is depleted during operation of the system. The object or apparatus may be single use, or may be replenished and used multiple times, for example, by refilling the object to replace the consumed material.

The term "bicarbonate feed" refers to fluid solution introduced into part of the dialysis or ultrafiltrate system. For example a "bicarbonate feed" is a conduit that contains a bicarbonate buffer concentrate that is used to readjust the pH of the dialysate.

The term "bidirectional pump" refers to a device configured to perform work on a fluid to cause the fluid to flow alternatively in either of two opposing directions.

A "biocompatible material" is a material that has the ability to interface with living biological tissues with an acceptable host response in any of specific medical systems, methods of treatment or delivery contemplated herein. The biocompatible material can consist of synthetic, natural or modified natural polymers intended to contact or interact with the biological systems during application of any of the inventions contained herein.

The term "bipolar electrodialysis system" refers to an electrochemical separation process in which ions are selectively transferred through a bipolar membrane.

The term "bipolar membrane" refers to a membrane formed by bonding an anion exchange and a cation exchange membrane together wherein the membranes result in the dissociation of water into hydrogen ions. The anion- and cation-exchange membranes can either be bound together physically or chemically such that the bipolar membrane has a thin interface where water diffuses into the membrane from outside aqueous salt solutions.

The term "blood access connection" refers to a junction or aperture through which the blood of a subject is conveyed to or from an extracorporeal circuit. Commonly, the blood access connection is made between a terminal end of a conduit of an extracorporeal circuit and the terminal end of a catheter or fistula needle that is distal to the subject receiving therapy. A subject may have more than one blood access connection when receiving therapy. In the case of two blood access connections they can be referred to as an arterial blood access connection and a venous blood access connection.

The term "blood solute" refers to a substance dissolved, suspended, or present in blood or dialysate.

The term "bolus" refers to an increase (or at times a decrease) of limited duration in an amount or concentration of one or more solutes, for example sodium, glucose and potassium, or a solvent, for example water, such that the concentration of a solution is changed. The term "bolus" includes delivery of solute and/or solvent to the dialysate fluid path such that it is delivered to the blood of a subject via diffusion and/or convection across a dialysis membrane such that the amount or concentration in the subject is increased or decreased. A "bolus" may also be delivered directly to the extracorporeal flow path or the blood of a subject without first passing through the dialysis membrane.

The term "bottled water" refers to water that may be filtered or purified and has been packaged in a container. Bottled water can include water that has been packaged and provided to a consumer as drinking water.

The term "breakthrough capacity" refers to the amount of solute a sorbent material can remove until breakthrough occurs. Breakthrough occurs when the concentration of a certain solute exiting a regeneration module becomes non-zero.

The terms "bubble detector," "bubble sensor," "gas detector" and "air detector" refer to a device that can detect the presence of a void, void space, or gas bubble in a liquid.

The term "buffer conduit flow path" refers to a fluid flow path in fluid communication with a stored source of a buffering material, such as bicarbonate.

The term "buffer source" refers to a stored material, such as bicarbonate, acetate or lactate that provides buffering.

The terms "buffer source container" and "buffer source cartridge" refer to objects that have or hold one or more materials, in solid and/or solution form, that are a source of buffering, for example a bicarbonate, a lactate, or acetate; and the object further having at least one port or opening to allow at least a portion of the buffering material to be released from the object during operation of the system.

The term "blood based solute monitoring system" refers to a system for monitoring a substance dissolved or suspended or present in blood or dialysate.

The term "blood rinse back" refers to returning the blood from a dialyzer and/or extracorporeal circuit to a subject, normally at conclusion of a therapy session and prior to disconnecting or removing the subject's blood access connection or connections. The procedure can include conveying a physiologically compatible solution through the extracorporeal circuit to push or flush the blood from the extracorporeal circuit to the subject via the subject's blood access connection or connections.

The terms "bypass circuit" "bypass conduit," "bypass flow path," "bypass conduit flow path" and "bypass" refer to a component or collection of components configured or operable to create an alternate fluid pathway to convey a fluid around one or more other components of a fluid circuit such that at least a portion of the fluid does not contact or pass through the one or more other components. At times the term "shunt" may be used interchangeable with the term "bypass." When any of the above "bypass" terms listed in this paragraph are used in context as being part of a controlled compliant system, then the relevant referenced "bypass" has the proper characteristics as to operate within a controlled compliant system as defined herein.

The term "bypass regulator" refers to a component such as valve that can determine the amount of fluid that can pass through a by-pass portion of a fluid circuit.

The term "capacitive deionization" refers to a process for directly removing salts from solution by applying an electric field between two electrodes.

The term "cartridge" refers to a compartment or collection of compartments that contains at least one material used for operation of the system of the present invention.

The term "cassette" refers to a grouping of components that are arranged together for attachment to, or use with the device, apparatus, or system. One or more components in a cassette can be any combination of single use, disposable, consumable, replaceable, or durable items or materials.

The term "cation exchange membrane" refers to a negatively charged membrane, which allows positively charged ions (cations) to pass. By convention, electrical current flows from the anode to the cathode when a potential is applied to an electrodialysis cell. Negatively charged anions such as chloride ions are drawn towards the anode, and positively charged cations such as sodium ions are drawn towards the cathode.

The term "cation infusate source" refers to a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid, non-limiting examples can be glucose, dextrose, acetic acid and citric acid.

The term "cation concentrate reservoir" refers to an object having or holding a substance that is comprised of at least one cation, for example calcium, magnesium, or potassium ions.

The terms "communicate" and "communication" include, but are not limited to, the connection of system electrical elements, either directly or remotely, for data transmission among and between said elements. The terms also include, but are not limited to, the connection of system fluid elements enabling fluid interface among and between said elements.

The terms "conduit," "conduit" or "flow path" refer to a vessel or passageway having a void volume through which a fluid can travel or move. A conduit can have a dimension parallel to the direction of travel of the fluid that is significantly longer than a dimension orthogonal to the direction of travel of the fluid.

The term "counter-current sorbent cartridge" refers to a sorbent cartridge as defined above that includes two inlet and two outlet flow paths. The first inlet and second inlet flow paths are on opposite ends of the sorbent cartridge along the direction of flow through the sorbent cartridge. Likewise, the first outlet and second outlet flow paths are on opposite ends of the sorbent cartridge along the direction of flow through the sorbent cartridge. The first inlet and second outlet are on the same end of the sorbent cartridge. Also, the first outlet and second inlet are on the same end of the sorbent cartridge.

The term "central axis" refers to (a) a straight line about which a body or a geometric figure rotates or may be supposed to rotate; (b) a straight line with respect to which a body or figure is symmetrical—called also axis of symmetry; (c) a straight line that bisects at right angles a system of parallel chords of a curve and divides the curve into two symmetrical parts; or (d): one of the reference lines of a coordinate system.

The term "chelating resins" refers to a class of resins that interacts and selectively binds with selected ions and ligands (the process is referred to as chelation). According to IUPAC, the formation or presence of two or more separate coordinate bonds.

The term "chronic kidney disease" (CKD) refers to a condition characterized by the slow loss of kidney function over time. The most common causes of CKD are high blood pressure, diabetes, heart disease, and diseases that cause inflammation in the kidneys. CKD can also be caused by infections or urinary blockages. If CKD progresses, it can lead to end-stage renal disease (ESRD), where the kidneys fail to function at a sufficient level.

The term "citric acid" refers to an organic acid having the chemical formula $C_6H_8O_7$, and may include anhydrous and hydrous forms of the molecule, and aqueous solutions containing the molecule.

The term "cleaning and/or disinfection concentrate" refers to a dry substance, or concentrated solutions containing at least one material for use in cleaning and/or disinfection of an apparatus.

The term "cleaning and/or disinfection solution" refers to a fluid that is used for the purpose of removing, destroying or impairing at least a portion of at least one contaminant. The contaminant may be organic, inorganic or an organism. The fluid may accomplish the purpose by transmission of thermal energy, by chemical means, flow friction or any combination thereof.

The terms "cleaning manifold" and "cleaning and disinfection manifold" refer to an apparatus that has fluid connection ports and one or more fluid pathways, or fluid port jumpers, that, when connected to jumpered ports of a base module, create one or more pathways for fluid to be conveyed between the jumpered ports of the base module. A cleaning manifold may be further comprised of additional elements, for example valves and reservoirs.

The term "container" as used herein is a receptacle that may be flexible or inflexible for holding fluid or solid, such as for example a spent dialysate fluid, or a sodium chloride or sodium bicarbonate solution or solid.

The terms "common container," "common cartridge," or "common reservoir," and the like refer to an object or apparatus that can hold more than one material; however, the time of holding more than one material may or may not necessarily be at the same time. The material(s) may be in solid and/or solution forms and may be held in separate compartments within the object or apparatus.

The term "common fluid inlet port" refers to an opening or aperture through which all fluid first passes to enter an object, apparatus or assembly.

The term "common fluid outlet port" refers to an opening or aperture through which all fluid passes to exit an object, apparatus or assembly.

The terms "communicate" and "communication" include, but are not limited to, the connection of system electrical elements, either directly or remotely, for data transmission among and between said elements. The terms also include, but are not limited to, the connection of system fluid elements enabling fluid interface among and between said elements.

The terms "component" and "components" refer to a part or element of a larger set or system. As used herein, a component may be an individual element, or it may itself be a grouping of components that are configured as a set, for example, as a cassette or a cleaning and/or disinfection manifold.

The term "comprising" includes, but is not limited to, whatever follows the word "comprising." Thus, use of the term indicates that the listed elements are required or mandatory but that other elements are optional and may or may not be present.

The term "concentrate pump" refers to a device that can perform work on a fluid solution to cause the fluid flow and can actively control the transfer of fluid volume such as an infusate or an acid concentrate, base concentrate, or buffer concentrate into a circuit.

The terms "concentrate flow channel," "concentrate flow loop," "concentrate stream," refer to a fluid line in which ion concentration is increased during electrodialysis.

The terms "conditioning conduit flow path" and "conditioning flow path" refer to a fluid pathway, circuit or flow loop that incorporates a source of a conditioning material, for example a sodium salt or bicarbonate.

The term "conditioning flow path inlet" refers to a location on a conditioning flow path where fluid enters the conditioning flow path The term "conditioning flow path outlet" refers to a location on a conditioning flow path where fluid exits the conditioning flow path.

The terms "conductivity meter," "conductivity sensor," "conductivity detector," conductivity electrode or the like, refer, in context, to a device for measuring the electrical conductance of a solution and/or the ion, such as a sodium ion, concentration of a solution. In specific examples, the conductivity sensor, meter, or conductor can be directed to a specific ion such as sodium and be referred to as a "sodium electrode," "sodium sensor," "sodium detector," or "sodium meter."

The term "conductive species" refers to a material's ability to conduct an electric current. Electrolytes are an example of a conductive species in dialysate fluids, such as, but not limited to the presence sodium, potassium, magnesium, phosphate, and chloride ions. A fluid's ability to conduct an electrical current is due in large part to the ions present in the solution. A fluid's ability to conduct an electrical current is due in large part to the ions present in the solution.

The terms "conduit," "circuit," and "flow path" refer to a vessel or passageway having a void volume through which a fluid can travel or move. A conduit can have a dimension parallel to the direction of travel of the fluid that is significantly longer than a dimension orthogonal to the direction of travel of the fluid.

The term "connectable" refers to being able to be joined together for purposes including but not limited to maintaining a position, allowing a flow of fluid, performing a measurement, transmitting power, and transmitting electrical signals. The term "connectable" can refer to being able to be joined together temporarily or permanently.

The term "consisting of" includes and is limited to whatever follows the phrase "consisting of." Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "consumables" refers to components that are dissipated, wasted, spent or used up during the performance of any function in the present invention. Examples include a quantity of sodium, bicarbonate, electrolytes, infusates, sorbents, cleaning and disinfecting ingredients, anticoagulants, and components for one or more concentrate solutions.

The terms "consumables cartridge" and "consumables container" refer to an object or apparatus having or holding one or more materials that are depleted during operation of the system. The one or more materials may be in solid and/or solution form and can be in separate compartments of the object or apparatus. The object or apparatus may be single use, or may be replenished and used multiple times, for example, by refilling the object to replace the consumed material.

The terms "contact," "contacted," and "contacting" refers, in context, to (1) a coming together or touching of objects, fluids, or surfaces; (2) the state or condition of touching or of immediate proximity; (3) connection or interaction. For example, in reference to a "dialysate contacting a sorbent material" refers to dialysate that has come together, has touched, or is in immediate proximity to connect or interact with any material or material layer of a sorbent container, system or cartridge.

The term "container" as used herein is a receptacle that may be flexible or inflexible for holding fluid or solid, such as for example a spent dialysate fluid, or a sodium chloride or sodium bicarbonate solution or solid, or the like.

The term "contaminant" refers to an undesirable or unwanted substance or organism that may cause impairment of the health of a subject receiving a treatment or of the operation of the system.

The term "control pump," such as for example an "ultrafiltrate pump," refers to a pump that is operable to pump fluid bi-directionally to actively control the transfer of fluid volume into or out of a compartment or circuit.

The terms "control reservoir," "ultrafiltrate reservoir," "solution reservoir," "therapy solution reservoir," and "waste reservoir," as the case may be, refers, in context, to a vessel or container, optionally accessible by a control pump that contains a variable amount of fluid, including fluid that can be referred to as an ultrafiltrate. These reservoirs can function as a common reservoir to store fluid volume from multiple sources in a system. Other fluids that can be contained by these reservoirs include, for example, water, priming fluids, waste fluids, dialysate, including spent dialysate, and mixtures thereof. In certain embodiments, the reservoirs can be substantially inflexible, or non-flexible. In other embodiments, the reservoirs can be flexible containers such as a polymer bag.

The term "control signals" refers to energy that is provided from one element of a system to another element of a system to convey information from one element to another or to cause an action. For example, a control signal can energize a valve actuator to cause a valve to open or close. In another example a switch on a valve can convey the open or close state of a valve to a controller.

A "control system" consists of combinations of components that act together to maintain a system to a desired set of performance specifications. The control system can use processors, memory and computer components configured to interoperate to maintain the desired performance specifications. It can also include fluid control components and solute control components as known within the art to maintain the performance specifications.

The terms "control valve" and "valve" refer to a device that can be operated to regulate the flow of fluid through a conduit or flow path by selectively permitting fluid flow, preventing fluid flow, modifying the rate of fluid flow, or selectively guiding a fluid flow to pass from one conduit or flow path to one or more other conduits or flow paths.

The terms "controlled compliant flow path," "controlled compliant dialysate flow path" and "controlled compliant solution flow path" refer to flow paths operating within a controlled compliant system having the characteristic of controlled compliance, or of being controlled compliant as defined herein.

A "controller," "control unit," "processor," or "microprocessor" is a device which monitors and affects the operational conditions of a given system. The operational conditions are typically referred to as output variables of the system wherein the output variables can be affected by adjusting certain input variables.

The terms "controlled compliance" and "controlled compliant" describe the ability to actively control the transfer of fluid volume into or out of a compartment, flow path or circuit. In certain embodiments, the variable volume of fluid in a dialysate circuit or controlled compliant flow path expands and contracts via the control of one or more pumps in conjunction with one or more reservoirs. The volume of fluid in the system is generally constant (unless additional fluids are added to a reservoir from outside of the system) once the system is in operation if the patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/or rebalanced fluids to the patient and optionally removing waste products. The terms "controlled compliance" and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In one embodiment, and as discussed herein and shown in the drawings is that the controlled compliant system can move fluids bi-directionally. In certain cases, the bi-directional fluid movement is across a semi-permeable membrane either inside or outside a dialyzer. The bi-directional fluid flow can also occur across, through, or between vessels, conduits, containers, flow paths, conditioning flow paths or cartridges of the invention in selected modes of operation. The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow path or between a flow path and reservoir in a controlled compliant system.

The terms "controlled compliant flow path," "controlled compliant dialysate flow path" and "controlled compliant solution flow path" refer to flow paths operating within a controlled compliant system having the characteristic of controlled compliance, or of being controlled compliant as defined herein.

The term "convective clearance" refers to the movement of solute molecules or ions across a semi-permeable barrier due to force created by solvent molecules moving across the semi-permeable barrier.

The terms "controller," "control unit," "processor," and "microprocessor" refers, in context, to a device which monitors and affects the operational conditions of a given system. The operational conditions are typically referred to as output variables of the system wherein the output variables can be affected by adjusting certain input variables.

The terms "coordinately operates" and "coordinately operating" refer to controlling the function of two or more elements or devices so that the combined functioning of the two or more elements or devices accomplishes a desired result. The term does not exclusively imply that all such elements or devices are simultaneously energized.

The term "deaeration" refers to removing some or all of the air contained in a liquid including both dissolved and non-dissolved air contained in the liquid.

The terms "de-aeration flow path" and "de-aeration flow path" refer to a set of elements that are configured in fluid communication along a fluid flow pathway such that a liquid can be passed through the fluid flow pathway to accomplish removal of some or all of the air or gas contained in the liquid, including removal of air or gas that is dissolved in the liquid.

The terms "degas module" and "degassing module" refer to a component that separates and removes any portion of one or more dissolved or undissolved gas from a liquid. A degas module can include a hydrophobic membrane for allowing ingress or egress of gases through a surface of the module while preventing the passage of liquid through that surface of the module.

The term "deionization resin" refers to any type of resin or material that can exchange one type of ion for another. In one specific case, the term can refer to the removal of ions such as potassium, magnesium, sodium and calcium in exchange for hydrogen and/or hydroxide ions.

The term "detachable" refers to a characteristic of an object or apparatus that permits it to be removed and/or disconnected from another object or apparatus.

The term "dialysate" describes a fluid into or out of which solutes from a fluid to be dialyzed diffuse through a membrane. A dialysate typically contains electrolytes that are close in concentration to the physiological concentration of electrolytes found in blood. A common sodium level for dialysate is approximately 140 mEq/L. Normal blood sodium levels range from approximately 135 mEq/L to 145 mEq/L. The REDY system typically uses dialysate ranging from 120 mEq/L to 160 mEq/L. In certain embodiment, a "predetermined limit" or "predetermined concentration" of sodium values can be based off the common sodium levels for dialysate and normal blood sodium levels. "Normal" saline at 0/9% by weight and commonly used for priming dialyzers and extracorporeal circuits is 154 mEq/L.

The terms "dialysate flow loop," "dialysate flow path," and "dialysate conduit flow path" refers, in context, to a fluid pathway that conveys a dialysate and is configured to form at least part of a fluid circuit for hemodialysis, hemofiltration, hemodiafiltration or ultrafiltration.

The terms "dialysate regeneration unit" and "dialysate regeneration system" refer to a system for removing certain electrolytes and waste species including urea from a dialysate after contact with a dialyzer. In certain instances, the component contained within the "dialysate regeneration unit" or "dialysate regeneration system" can decrease the concentration or conductivity of at least one ionic species, or release and/or absorb at least one solute from a dialysate.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The terms "dialysis membrane," "hemodialysis membrane," "hemofiltration membrane," "hemodiafiltration membrane," "ultrafiltration membrane," and generally "membrane," refer, in context, to a semi-permeable barrier selective to allow diffusion and convection of solutes of a specific range of molecular weights through the barrier that separates blood and dialysate, or blood and filtrate, while allowing diffusive and/or convective transfer between the blood on one side of the membrane and the dialysate or filtrate circuit on the other side of the membrane.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly (methyl methacrylate), modified cellulose, or other materials known to those skilled in the art.

"Diffusive permeability" is a property of a membrane describing permeation by diffusion. Diffusion is the process of solutes moving from an area of higher concentration to an area of lower concentration.

The terms "diluate flow channel," "feed stream," "diluate stream," and the like, refer, in context, to a fluid line of solution entering an electrodialysis cell or electrodialysis unit wherein the ion concentration in the fluid solution is changed.

The terms "diluent" and "diluate" refer to a fluid having a concentration of a specific species less than a fluid to which the diluent is added.

A "disc electrode" consists of an electrode with an electrode head in the shape of a disc. A "rod electrode" refers to an electrode in the shape of a rod or cylinder, with one end functioning as an electrode head. A "sheet electrode" refers to an electrode with an electrode head in the shape of a sheet. The sheet can be square, rectangular, circular or other solid planar geometries. A "mesh electrode" refers to an electrode with an electrode head consisting of a mesh, where a mesh is the same as that described for a mesh electrode. An "antenna electrode" refers to an electrode with an electrode head in the shape of an antenna, where antenna shape refers to a serpentine structure of conductive wires or strips. A "pin electrode refers" to a rod electrode with a small diameter. Other electrode and electrode head geometries can be considered.

The term "disinfection fluid" refers to a solution for use in cleaning and disinfecting an apparatus for hemodialysis, hemodiafiltration or hemofiltration. The disinfection fluid may act thermally, chemically, and combinations thereof to inhibit growth of or to destroy microorganisms. The "disinfection fluid" may further act to remove, at least in part, a buildup of microorganisms on a surface of a fluid flow path, such buildups of microorganisms may be commonly referred to as a biofilm.

The terms "diverted sample stream" and "diverting a sample stream" refer redirecting part of a fluid from the main flow path to accomplish another purpose, such as to measure a fluid characteristic, remove a portion of the fluid stream in order to take a sample. More than one sample stream may be diverted, such as a "first sample stream, "second sample stream," "third sample stream," "fourth sample stream," and the like.

The term "dry" as applied to a solid or a powder contained in a cartridge means not visibly wet, and may refer interchangeably to anhydrous and also to partially hydrated forms of those materials, for example, monohydrates and dihydrates.

The term "downstream" refers to a direction in which a moving dialysate or other fluid moves within a conduit or flow path.

The term "downstream conductivity" refers to the conductivity of a fluid solution as measured at a location of a fluid flow path in the direction of the normal fluid flow from a reference point.

The term "drain connection" refers to being joined in fluid communication with a conduit or vessel that can accept fluid egress from the system.

The term "dry composition" refers to a compound that does not contain a substantial quantity of water and can include anhydrous forms as well as hydrates for example, monohydrates and dihydrates.

The term "effluent dialysate," as used herein describes the discharge or outflow after the dialysate has been used for dialysis.

The term "electrode" as used herein describes an electrical conductor used to make contact with a part of a fluid, a solid or solution. For example, electrical conductors can be used as electrodes to contact any fluid (e.g. dialysate) to measure the conductivity of the fluid or deliver or receive charge to the fluid. A "disc electrode" consists of an electrode with an electrode head in the shape of a disc. A "rod electrode" refers to an electrode in the shape of a rod or cylinder, with one end functioning as an electrode head. A "sheet electrode" refers to an electrode with an electrode head in the shape of a sheet. The sheet can be square, rectangular, circular or other solid planar geometries. A "mesh electrode" refers to an electrode with an electrode head consisting of a mesh, where a mesh is the same as that described for a mesh electrode. An "antenna electrode" refers to an electrode with an electrode head in the shape of an antenna, where antenna shape refers to a serpentine structure of conductive wires or strips. A "pin electrode" refers to a rod electrode with a small diameter. Other electrode and electrode head geometries can be considered.

The term "electrode array" refers to an array of one or more electrodes contained in an insulator substrate. The insulator substrate can be rigid or flexible and acts to isolate the electrodes from each other. A non-limiting example of an "electrode array" is a flex-circuit, which is a flexible circuit board containing electrodes.

The term "electrode head" refers to the portion of an electrode that is in physical contact with a fluid, that conductivity is to be measured from.

The terms "electrode rinse" and "electrode rinse solution" refer to any suitable solution such as sodium sulfate solution that prevents undesirable oxidation and flushes reactants from an electrode surface.

The terms "electrode rinse flow channel," "electrode rinse stream," and the like refer to a fluid line of an electrode rinse or "electrode rinse solution."

The term "electrode rinse reservoir" refers to a vessel or container for holding the electrode rinse or electrode rinse solution. The reservoir may have an inflexible or flexible volume capacity.

The term "electrodialysis" refers to an electrically driven membrane separation process capable of separating, purifying, and concentrating desired ions from aqueous solutions or solvents.

The term "electrodialysis cell" refers to an apparatus having alternating anion- and cation-exchange membranes that can perform electrodialysis using an electrical driving force between an anode and cathode housed at opposite ends of the cell. The cell consists of a diluate compartment fed by a diluate stream and a concentrate compartment fed by a concentrate stream. One or more electrodialysis cells can be multiply arranged to form an "electrodialysis stack."

The term "electrolyte" refers to an ion or ions dissolved in an aqueous medium, including but not limited to sodium, potassium, calcium, magnesium, acetate, bicarbonate, and chloride.

The terms "electrolyte source" and "electrolyte source" refer to a stored substance that provides one or more electrolytes.

The terms "equilibrated," "equilibrate," "to equilibrate," and the like, refer to a state where a concentration of a solute in a first fluid has become approximately equal to the concentration of that solute in the second fluid. However, the term equilibrated as used herein does not imply that the concentration of the solute in the first fluid and the second fluid have become equal. The term can also be used in reference to the process of one or more gases coming into equilibrium where the gases have equal pressures or between a liquid and a gas.

The term "equilibrated to the solute species concentration" refers to more specifically where a concentration of a particular solute species in a first fluid has become approximately equal to the concentration of that solute species in the second fluid. The concentration need not be exact.

The terms "evacuation volume," "priming volume" and "void volume" refer to the internal volume of a component or collection of components comprising a fluid flow path and are the volume of fluid that can be removed from the fluid flow path to empty the fluid flow path if it has been filled with fluid.

The term "extracorporeal," as used herein generally means situated or occurring outside the body.

The term "extracorporeal circuit" refers to a fluid pathway incorporating one or more components such as, but not limited to, conduits, valves, pumps, fluid connection ports or sensing devices configured therein such that the pathway conveys blood from a subject to an apparatus for hemodialysis, hemofiltration, hemodiafiltration or ultrafiltration and back to the subject.

The terms "extracorporeal flow path pump" and "blood pump" refer to a device to move or convey fluid through an extracorporeal circuit. The pump may be of any type suitable for pumping blood, including those known to persons of skill in the art, for example peristaltic pumps, tubing pumps, diaphragm pumps, centrifugal pumps, and shuttle pumps.

The term "feed solution" refers to a dialysate or ultrafiltrate fluid solution introduced into part of the dialysis or ultrafiltrate system. For example a "feed solution" can refer to a dialysate or ultrafiltrate fluid solution introduced to an electrodialysis cell.

The term "filtering media" refers to a material that can allow a fluid to pass through, but which inhibits passage of non-fluid substances that are larger than a predetermined size.

The terms "filtrate regeneration unit" and "filtrate regeneration system" refer to a system for removing certain electrolytes and waste species including urea from a filtrate produced using filtration.

The terms "filtrate regeneration circuit," "filtrate regeneration loop," and the like, refer to a flow path containing fluid resulting from filtration; for the removal of certain electrolytes and waste species including urea.

The term "filtration" refers to a process of separating solutes from a fluid, by passing the fluid through a filter medium across which certain solutes or suspensions cannot pass. Filtration is driven by the pressure difference across the membrane.

The term "first terminal end" of a flow path refers to one end of the flow path and "second terminal end" refers to another end of the flow path. Neither the "first terminal end" nor the "second terminal end" has any limitation on placement on an arterial or venous side.

The term "first terminal valve" refers to a valve substantially located at one end of a first fluid conduit without any requirement that the valve be place on an arterial or venous side. Similarly, the term "second terminal valve" refers to a valve substantially located at one end of a second fluid conduit and so on without any limitation on placement on an arterial or venous side.

The term "flow loop" refers to a grouping of components that may guide the movement of a fluid, convey the fluid, exchange energy with the fluid, modify the composition of the fluid, measure a characteristic of the fluid and/or detect the fluid. A flow loop comprises a route or a collection of routes for a fluid to move within. Within a flow loop there may be more than one route that a volume of fluid can follow to move from one position to another position. A fluid volume may move through a flow loop such that it recirculates, or passes the same position more than once as it moves through a flow loop. A flow loop may operate to cause fluid volume ingress to and fluid volume egress from the flow loop. The term "flow loop" and "flow path" often may be used interchangeably. Further types of flow paths may be further defined; for example, (1) a recirculation flow path, would be a flow path whose function is in whole or part is to recirculate fluid through the defined flow path; (2) a dialyzer recirculation flow path would be a flow path whose function is in whole or part is to recirculate fluid through the defined flow path having a dialyzer' (3) a controlled compliant flow path would be a flow path would be a flow path that is controlled compliant as defined herein. Any of the defined flow paths may be referred to numerically, as a first flow path, second, third flow path, or fourth flow path, and the like flow paths.

The term "flow path" refers to a route or a collection of routes for a fluid to move within. Within a flow path there may be more than one route that a fluid can follow to move from a first position to a second position. A fluid may move through a flow path such that it recirculates, or passes the same position more than once as it moves through a flow path. A flow path may be a single element such as a tube, or a flow path may be a grouping of components of any type that guide the movement of a fluid. The term "flow loop" and "flow path" often may be used interchangeably.

The term "fluid communication" refers to the ability of fluid to move from one component or compartment to another within a system or the state of being connected, such that fluid can move by pressure differences from one portion that is connected to another portion.

"Hemodiafiltration" is a therapy that combines hemofiltration and hemodialysis.

"Hemofiltration" is a therapy in which blood is filtered across a semi-permeable membrane. Water and solutes are removed from the blood via pressure-driven convection across the membrane. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates. In hemofiltration, solutes small enough to pass through the membrane in proportion to their plasma concentration are removed. The driving force is a pressure gradient rather than a concentration gradient. A positive hydrostatic pressure drives water and solutes across the filter membrane from the blood compartment to the filtrate compartment, from which it is drained. Solutes, both small and large, get dragged through the membrane at a similar rate by the flow of water that has been engineered by the hydrostatic pressure. Hence, convection overcomes the reduced removal rate of larger solutes (due to their slow speed of diffusion) observed in hemodialysis. The rate of solute removal is proportional to the amount of fluid removed from the blood circuit, which can be adjusted to meet the needs of a clinical situation. In general, the removal of large amounts of plasma water from the patient requires volume substitution. Substitution fluid, typically a buffered solution close to the plasma water composition a patient needs, can be administered pre or post filter (pre-dilution mode, post-dilution mode).

"Hemodialysis" is a technique where blood and a "cleansing fluid" called dialysate are exposed to each other separated by a semi-permeable membrane. Solutes within the permeability range of the membrane pass while diffusing along existing concentration gradients. Water and solutes are also transferred by convection across a pressure gradient that may exist across the dialysis membrane. The dialysate employed during hemodialysis has soluble ions such as sodium, calcium and potassium ions and is not pure water. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates.

The term "hemofilter" refers to a apparatus (or may refer to a filter) used in hemofiltration. A hemofilter apparatus can be connected to an extracorporeal circuit and configured to operate with a semipermeable membrane that separates at least a portion of the fluid volume from blood to produce a filtrate fluid.

The term "horizontal to a central axis" refers to a relative position of components such as sensors that can be placed in a plane having portions generally horizontal to the central axis.

The term "hydrophobic membrane" refers to a semipermeable porous material that may allow gas phases of matter to pass through, but which substantially resists the flow of water through the material due to the surface interaction between the water and the hydrophobic material.

The terms "hydrophobic vent" and "hydrophobic vent membrane" refer to a porous material layer or covering that can resist the passage of a liquid such as water through the pores while allowing the passage of a gas. The pores may also be of a sufficiently small size to substantially prevent the passage of microorganisms.

"Hemodiafiltration" is a therapy that combines hemofiltration and hemodialysis.

The term "perpendicular to a central axis" refers to the position of components, e.g. sensors that can be placed in a plane having portions generally perpendicular to the central axis.

The term "in contact" as referred to herein denotes (a) a coming together or touching, as of objects or surfaces; or (b) the state or condition of touching or of being in immediate proximity. "In contact" also includes fluids that are "in fluid communication with" with a solid, such as for example, a fluid, like a dialysate, in contact with a material layer of a sorbent cartridge, or a fluid in contact with a sensor.

The term "impedance meter" refers to a device for measuring the opposition of an object or structure to an alternating current.

The term "impurity species" refers to solutes in the blood that are in too high of a concentration in the blood from standard ranges known in the art or that are solutes that have resulted from metabolism to generate a non-healthy component now residing in the blood. An "impurity species" is one which is also regarded as a "waste species," or "waste products".

The term "ion selective electrode" refers to electrodes coated with a material that only allows certain ions to pass through. An "ion selective electrode" (ISE), also known as a specific ion electrode (SIE), is a transducer (or sensor) that converts the activity of a specific ion dissolved in a solution into an electrical potential, which can be measured by a voltmeter or pH meter. The voltage is theoretically dependent on the logarithm of the ionic activity, according to the Nernst equation. The sensing part of the electrode is usually made as an ion-specific membrane, along with a reference electrode.

The terms "infusate container" and "infusate reservoir" refer to a vessel, which can be substantially inflexible or non-flexible for holding a solution of one or more salts for the adjustment of the composition of a dialysate.

The term "infusate solution" refers to a solution of one or more salts for the adjustment of the composition of a dialysate, such as salts of calcium, magnesium, potassium, and glucose.

The term "infusate system" refers to a system that incorporates at least one fluid pathway including components such as conduits, valves, pumps or fluid connection ports, an infusate container or a controller configured to add an infusate solution to the dialysate.

The term "interchangeable bicarbonate cartridge" refers to a bicarbonate cartridge that can be configured for removal and replacement with a like bicarbonate cartridge. Interchangeable bicarbonate cartridges can be single use disposable, or re-fillable, re-usable containers.

The term "interchangeable sodium chloride cartridge" refers to a sodium chloride cartridge that can be configured for removal and replacement with a like sodium chloride cartridge. Interchangeable sodium chloride cartridges can be single use disposable, or re-fillable, re-usable containers.

The terms "introduce" and "introducing" refer to causing a substance to become present where it was not present, or to cause the amount or concentration of a substance to be increased.

The term "ion-exchange material" refers to any type of resin or material that can exchange one type of ion for another. The "ion-exchange material" can include anion and cation exchange materials. In one specific case, the term can refer to the removal of ions such as potassium, magnesium, sodium, phosphate and calcium in exchange for other ions such as potassium, sodium, acetate, hydrogen and/or hydroxide.

An "ion-exchange resin" or "ion-exchange polymer" is an insoluble matrix (or support structure) that can be in the form of small (1-2 mm diameter) beads, fabricated from an organic polymer substrate. The material has a developed structure of pores on the surface of which are sites with easily trapped and released ions. The trapping of ions takes place only with simultaneous releasing of other ions; thus the process is called ion-exchange. There are multiple different types of ion-exchange resin which are fabricated to selectively prefer one or several different types of ions. In one specific case, the term can refer to the removal of ions such as potassium, magnesium, sodium, phosphate and calcium in exchange for other ions such as potassium, sodium, acetate, hydrogen and/or hydroxide.

The term "ion selective electrode" (ISE), also known as a specific ion electrode (SIE), is a transducer (or sensor) that converts the activity of a specific ion dissolved in a solution into an electrical potential, which can be measured by a voltmeter or pH meter. The voltage is theoretically dependent on the logarithm of the ionic activity, according to the Nernst equation. The sensing part of the electrode is usually made as an ion-specific membrane, along with a reference electrode.

The term "junction" refers to a common point of connection between two or more flow paths or conduits that allows a liquid and/or a gas to move from one pathway or conduit to another. A junction may be a reversible connection that can be separated when transfer of a liquid and/or gas between the flow paths or conduits is not needed.

The term "kidney replacement therapy" as used herein describes the use of a provided system to replace, supplement, or augment the function of a patient with impaired kidney function, such as would occur for a patient with Chronic Kidney Disease. Examples of kidney replacement therapy would include dialysis, hemofiltration, hemodialysis, hemodiafiltration, peritoneal dialysis, and the like.

The terms "luer connector" and "luer adapter" refer to adapters or connectors conforming to International Standards Organization (ISO) standards 594-2.

The term "manifold" refers to a collection of one or more fluid pathways that are formed within a single unit or subassembly. Many types of manifolds can be used, e.g. a cleaning and/or disinfecting manifold is used to clean or disinfect the defined flow loop when the flow loop is connected to the cleaning and/or disinfecting manifold.

The term "material layer" refers to the layers of materials found in a sorbent cartridge. The material layers in a sorbent cartridge may have one or more layers selected from a urease-containing material, alumina, zirconium phosphate, zirconium oxide, and activated carbon.

The term "memory" refers to a device for recording digital information that can be accessed by a microprocessor, such as RAM, Dynamic RAM, microprocessor cache, FLASH memory, or memory card.

The term "mesh electrode" refers to an electrode in the shape of a mesh, where a mesh consists of a planar structure with openings. The mesh can be made from; overlapping wires or strips, a sheet machined or manufactured to contain holes or openings, or a sheet with a permeable, porous structure. In all cases the mesh is manufactured from materials that result in electrodes, such as titanium, platinum, stainless steel, and iridium. In the case of an electrode mesh consisting of overlapping wires or strips, certain wires or strips can be isolated from other wires or strips with an insulator material in order to apply one polarity to certain wires or strips and the opposite polarity to other wires or strips.

The term "metabolic waste species," as used herein describes organic and inorganic components generated by a patient. They can be metabolic products such as urea, uric acid, creatinine, chlorides, inorganic sulfates and phosphate, or excess electrolytes such as sodium, potassium, etc. It will be understood that the specific "metabolic waste species" can vary between individuals depending on diet and environmental factors. Hence, the term is intended to encompass any waste component that is normally removed by a kidney or by dialysis without restriction on the specific type of waste substance.

The term "mid-weight uremic wastes" refers to uremic wastes that can pass through a dialysis membrane and have a molecular weight less than about 66,000 g/mol and greater than about 1000 g/mol. An example of a middle molecule is beta-2 microglobulin.

The term "mixing chamber" refers to a chamber or vessel, with one or more inlet and outlet fluid streams, that provides mixing between the fluid streams entering the chamber.

The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow loop in a controlled compliant system.

A multiplexer" or "mux" is an electronic device that selects one of several analog or digital input signals and forwards the selected input into a single line.

The term "nitrogenous waste" refers to any non-polymeric nitrogen-containing organic compound originating from the blood of a patient. Nitrogenous waste includes urea and creatinine, which are both "waste species."

The term "one-way valve" refers to a device that allows flow to pass in one direction through the valve, but prevents or substantially resists flow through the valve in the opposite direction. Such devices can include devices commonly referred to as check valves "Osmolarity" is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

The term "parallel or wound hollow fiber assembly" refers to any device that incorporates a porous or non-porous hollow fiber material that allows a gas to pass through the material wall of the hollow fibers, but resists the passage of a liquid through the material wall and is configured as multiple strands aligned in parallel or wrapped around a core. The liquid to be degassed may be conveyed through either the inside of the hollow fibers or around the outside of the hollow fibers. Optionally, a gas may be conveyed on the side of the material wall that is opposite the liquid to be degassed. Optionally, a vacuum may be applied on the side of the material wall that is opposite the liquid to be degassed.

A "patient" or "subject" is a member of any animal species, preferably a mammalian species, optionally a human. The subject can be an apparently healthy individual, an individual suffering from a disease, or an individual being treated for a disease.

The term "parallel to a central axis" refers to the position of components, e.g. sensors that can be placed in a plane having portions generally parallel to the central axis.

The terms "pathway," "conveyance pathway" and "flow path" refer to the route through which a fluid, such as dialysate or blood travels.

The term "patient fluid balance" refers to the amount or volume of fluid added to or removed from a subject undergoing a treatment.

The term "peristaltic pump" refers to a pump that operates by compression of a flexible conduit or tube through which the fluid to be pumped passes.

The term "perpendicular to a central axis" refers to the position of components, e.g. sensors that can be placed in a plane having portions generally perpendicular to the central axis.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient.

The term "pH-buffer modifying solution" refers to a solution that can reduce the acidity (pH) of the working dialysate solution when added to the dialysate The term "pH-buffer sensor" refers to a device for measuring the acidity or basicity (pH) and the buffer concentration of the dialysate solution.

The term "pH-buffer management system" refers to a system managing the pH and buffer concentration of a dialysate by adding, removing or generating a fluid to the dialysate such that the dialysate is modified by the pH-buffer management system to have a different pH and buffer concentration.

The term "pH-buffer measurement system" refers to a system measuring the pH and/or buffer concentration of a dialysate or fluid within the system.

The terms "portable system" and "wearable system" refers to a system in whole or in part having a mass and dimension to allow for transport by a single individual by carrying the system or wearing the system on the individual's body. The terms are to be interpreted broadly without any limitation as to size, weight, length of time carried, comfort, ease of use, and specific use by any person whether man, woman or child. The term is to be used in a general sense wherein one of ordinary skill will understand that portability as contemplated by the invention encompasses a wide range of weights, geometries, configurations and size.

The term "potable water" refers to drinking water or water that is generally safe for human consumption with low risk of immediate or long term harm. The level of safety for human consumption can depend on a particular geography where water safe for human consumption may be different from water considered safe in another jurisdiction. The term does not necessarily include water that is completely free of impurities, contaminants, pathogens or toxins. Other types of water suitable for use in the present invention can include purified, deionized, distilled, bottled drinking water, or other pre-processed water that would be understood by those of ordinary skill in the art as being suitable for use in dialysis.

The term "potassium-modified fluid" refers to fluid having a different conductivity or potassium concentration compared to a second fluid to which the potassium-modified fluid is added to modify the conductivity or potassium concentration of the second fluid.

The terms "physiologically compatible fluid" and "physiological compatible solution" refer to a fluid that can be safely introduced into the bloodstream of a living subject.

The term "plumbing," as used herein generally describes any system of valves, conduits, channels, and lines for supplying any of the fluids used in the invention.

The term "porosity," as used herein describes the fraction of open pore volume of a membrane.

The terms "pressure differential" and "pressure drop" refer to the difference in pressure measurements of a fluid between two points of measurement.

The terms "pressure meter" and "pressure sensor" refer to a device for measuring the pressure of a gas or liquid in a vessel or container.

The terms "priming process" and "priming" refer to the process of conveying a liquid into the void volume of a fluid pathway to fill the pathway with liquid.

The term "priming volume" refers to the volume of priming fluid required to fill the void volume of the subject pathway, device, or component, as the particular case may be.

The term "priming overflow reservoir" refers to a reservoir which during priming is used to collect the overflow of fluid during the priming process.

The terms "processor," "computer processor," and "microprocessor" as used herein are broad terms and are to be given their ordinary and customary meaning to a person of ordinary skill in the art. The terms refer without limitation to a computer system, state machine, processor, or the like designed to perform arithmetic or logic operations using logic circuitry that responds to and processes the basic instructions that drive a computer. In some embodiments, the terms can include ROM ("read-only memory") and/or RAM ("random-access memory") associated therewith.

The term "programmable" as used herein refers to a device using computer hardware architecture with a stored program and being capable of carrying out a set of commands, automatically that can be changed or replaced.

The term "pump" refers to any device that causes the movement of fluids or gases by the application of suction or pressure.

The term "pulsatile pump" refers to a pump where the pumped fluid undergoes periodic variation in velocity and/or pressure.

The terms "pump rate" and "volumetric pumping rate" refer to the volume of fluid that a pump conveys per unit of time.

The term "purified water" refers to water that has been physically processed to remove at least a portion of at least one impurity from the water.

The term "outlet stream" refers to a fluid stream exiting a chamber, vessel or cartridge.

The terms "reconstitute" and "reconstituting" refer to creating a solution by addition of a liquid to a dry material or to a solution of higher concentration to change the concentration level of the solution. A "reconstitution system" in one use, is a system that rebalances the dialysate in the system to ensure it contains the appropriate amount of electrolytes and buffer.

The term "refilled" refers to having replenished or restored a substance that has been consumed or degraded.

The terms "sorbent regeneration," "sorbent regeneration system," "sorbent system, and the like, refer, in context, to devices that are part of a sorbent regenerated dialysate delivery system for hemodialysis, functioning as an artificial kidney system for the treatment of patients with renal failure or toxemic conditions, and that consists of a sorbent cartridge and the means to circulate dialysate through this cartridge and the dialysate compartment of the dialyzer. The device is used with the extracorporeal blood system and the dialyzer of the hemodialysis system and accessories. The device may include the means to maintain the temperature, conductivity, electrolyte balance, flow rate and pressure of the dialysate, and alarms to indicate abnormal dialysate conditions. The sorbent cartridge may include absorbent, ion exchange and catalytics.

The term "shunt," as most often used herein describes a passage between channels, in the described filtration and purification systems, wherein the shunt diverts or permits flow from one pathway or region to another. An alternate meaning of "shunt" can refer to a pathway or passage by which a bodily fluid (such as blood) is diverted from one channel, circulatory path, or part to another. The term "bypass" can often be used interchangeably with the term "shunt."

The term "sodium-concentrate solution" refers to a solution having a high concentration of sodium ions relative to another solution or fluid.

The terms "sodium chloride cartridge" and "sodium chloride container" refer to an object that can be a stand-alone enclosure or alternatively can be integrally formed with an apparatus for hemodialysis, hemodiafiltration, or hemofiltration. The object can store a source of sodium, such as sodium chloride in solid and/or solution form, and can be configured to interface with at least one other functional module found in systems for hemodialysis, hemodiafiltration, or hemofiltration. For example, the sodium chloride cartridge or container can contain at least one fluid pathway and include components such as conduits, valves, filters or fluid connection ports.

The term "regenerative capacity of the sorbent" refers to the remaining capacity for the sorbent cartridge or a particular material layer of the sorbent cartridge to perform its intended function.

The term "regenerative substance" refers to a sorbent material contained in a "regeneration module." The term "first chosen regenerative substance," as used in the present invention refers to a particular regenerative substance, identified as "first chosen regenerative substance." The term "second chosen regenerative substance" refers to a particular regenerative substance, identified as "second chosen regenerative substance."

The term "regeneration module" refers to an enclosure having one or more sorbent materials for removing specific solutes from solution, such as urea. In certain embodiments, the term "regeneration module" includes configurations where at least some of the materials contained in the module do not act by mechanisms of adsorption or absorption.

The terms "remnant volume" and "residual volume" refer to the volume of fluid remaining in a fluid flow path after the fluid flow path has been partially emptied or evacuated.

The terms "replacement fluid" and "substitution fluid" refer to fluid that is delivered to the blood of a subject undergoing convective renal replacement therapies such as hemofiltration or hemodiafiltration in order to replace at least a portion of the fluid volume that is removed from the subject's blood when the blood is passed through a hemofilter or a dialyzer.

The term "reserve for bolus infusion" refers to an amount of solution available, if needed, for the purpose of administering fluid to a subject receiving therapy, for example, to treat an episode of intradialytic hypotension.

The term "reusable" refers to an item that is used more than once. Reusable does not imply infinitely durable. A reusable item may be replaced or discarded after one or more use.

The term "reverse osmosis" refers to a filtration method of forcing a solvent from a region of high solute concentration through a semipermeable membrane to a region of low solute concentration by applying a pressure in excess of osmotic pressure. To be "selective," this membrane should not allow large molecules or ions through the pores (holes), but should allow smaller components of the solution (such as the solvent) to pass freely.

The term "reverse osmosis rejection fraction" refers to the resulting solute that is retained on the pressurized side of the membrane and the pure solvent is allowed to pass to the other side in a reverse osmosis system.

The term "reversible connections" refers to any type of detachable, permanent or non-permanent connection configured for multiple uses.

The term "salination pump" refers to a pump configured to move fluid and/or control movement of fluid through a conditioning flow path, such as through or from a source of a conditioning material such as sodium chloride or sodium bicarbonate.

The term "salination valve" refers to a valve configured to control the flow of fluid in a conditioning flow path, such as through or from a source of a conditioning material such as sodium chloride or sodium bicarbonate.

The term "segment" refers to a portion of the whole, such as a portion of a fluid flow path or a portion of a fluid circuit. A segment is not limited to a tube or conduit, and includes any grouping of elements that are described for a particular segment. Use of the term "segment," by itself, does not imply reversible or detachable connection to another segment. In any embodiment, a segment may be permanently connected to one or more other segments or removably or detachably connected to one or more segments.

The terms "selectively meter fluid in" and "selectively meter fluid out" generally refer to a process for controllably transferring fluids from one fluid compartment (e.g. a selected patient fluid volume, flow path, or reservoir) to another fluid compartment. One non-limiting example is where a control pump may transfer a defined fluid volume container, reservoirs, flow paths, conduit of the controlled compliant system. When fluid is moved from a reservoir into another part of the system, the process is referred to as "selectively metering fluid in" as related to that part of the system. Similarly, one non-limiting example of removing a defined volume of dialysate from a dialysate flow path in a controlled compliant system and storing the spent dialysate in a control reservoir can be referred to as "selectively metering-out" the fluid from the dialysate flow path.

The terms "semipermeable membrane," "selectively permeable membrane," "partially permeable membrane," and "differentially permeable membrane," refer to a membrane that will allow certain molecules or ions to pass through it by diffusion and occasionally specialized "facilitated diffusion". The rate of passage depends on the pressure, concentration, and temperature of the molecules or solutes on either side, as well as the permeability of the membrane to each solute. The term "semi-permeable membrane" can also refer to a material that inhibits the passage of larger molecular weight components of a solution while allowing passage of other components of a solution having a smaller molecular weight. For example, Dialyzer membranes come with different pore sizes. Those with smaller pore size are called "low-flux" and those with larger pore sizes are called "high-flux." Some larger molecules, such as beta-2-microglobulin, are not effectively removed with low-flux dialyzers. Because beta-2-microglobulin is a large molecule, with a molecular weight of about 11,600 daltons, it does not pass effectively through low-flux dialysis membranes.

The term "sensor," which can also be referred to as a "detector" in certain instances, as used herein can be a converter that measures a physical quantity of a matter in a solution, liquid or gas, and can convert it into a signal which can be read by an electronic instrument.

The term "sensor element" refers to a device or component of a system that detects or measures a physical property.

The terms "sodium management system" and "sodium management" broadly refer to a system or process that can maintain the sodium ion concentration of a fluid in a desired range. In certain instances, the desired range can be within a physiologically-compatible range. The sodium ion concentration of an input solution can be modified by any means including application of an electrical field.

The term "sodium-modified fluid" refers to fluid having a different conductivity or sodium concentration compared to a second fluid to which the sodium-modified fluid is added to modify the conductivity or sodium concentration of the second fluid.

The term "sodium conduit flow path" refers to a flow path in fluid communication with a sodium chloride cartridge which then can pump saturated sodium solution into the dialysate by pumping and metering action of a salination pump.

The term "sodium source" refers to a source from which sodium can be obtained. For example, the sodium source can be a solution containing sodium chloride or a dry sodium chloride composition that is hydrated by the system.

The term "solid potassium" refers to a solid composition containing a salt of potassium such as potassium chloride at any purity level. In general, the solid potassium will be easily soluble in water to form a solution.

The term "solid sodium" refers to a solid composition containing a salt of sodium such as sodium chloride at any purity level. In general, the solid potassium will be easily soluble in water to form a solution and of high purity.

The term "solid bicarbonate" refers to a composition containing a salt of bicarbonate such as sodium bicarbonate at any purity level. In general, the solid bicarbonate will be easily soluble in water to form a solution.

The term "solute" refers to a substance dissolved, suspended, or present in another substance, usually the component of a solution present in the lesser amount.

The terms "sorbent cartridge" and "sorbent container" refer to a cartridge containing one or more sorbent materials for removing specific solutes from solution, such as urea. The term "sorbent cartridge" does not necessarily require the contents in the cartridge be sorbent based. In this connection, the sorbent cartridge may include any suitable amount of one or more sorbent materials. In certain instances, the term "sorbent cartridge" refers to a regeneration cartridge which includes one or more sorbent materials in addition to one or more other regeneration materials. "Sorbent cartridge" includes configurations where at least some of the materials contained in the cartridge do not act by mechanisms of adsorption or absorption.

The terms "sorbent regeneration," "sorbent regeneration system," "sorbent system, and the like, refer, in context, to devices that are part of a sorbent regenerated dialysate delivery system for hemodialysis, functioning as an artificial kidney system for the treatment of patients with renal failure or toxemic conditions, and that consists of a sorbent cartridge and the means to circulate dialysate through this cartridge and the dialysate compartment of the dialyzer. The device is used with the extracorporeal blood system and the dialyzer of the hemodialysis system and accessories. The device may include the means to maintain the temperature, conductivity, electrolyte balance, flow rate and pressure of the dialysate, and alarms to indicate abnormal dialysate conditions. The sorbent cartridge may include absorbent, ion exchange and catalytics.

The term "source of cations" refers a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid. Non-limiting examples include glucose, dextrose, acetic acid and citric acid.

The term "specified gas membrane permeability" refers to a determined rate at which a gas membrane will allow a gas to pass through the membrane from a first surface to a second surface, the rate being proportional to the difference in absolute pressure of the gas in proximity to the first side of the membrane and in proximity to the second side of the membrane.

The term "spent dialysate" refers to a dialysate that has been contacted with blood through a dialysis membrane and contains one or more impurity, or waste species, or waste substance, such as urea.

The term "static mixer" refers to a device that mixes two or more component materials in a fluid solution without requiring the use of moving parts.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Once a substantially inflexible volume has been filled with a fluid, removal of fluid from that volume will create a negative pressure that resists fluid removal unless fluid is added and removed simultaneously at substantially equal rates. Those skilled in the art will recognize that a minimal amount of expansion or contraction of the vessel or container can occur in a substantially inflexible volume; however, the addition or subtraction of a significant volume of fluid over a maximum or minimum will be resisted.

The term "tap water" refers to water, as defined herein, from a piped supply.

The term "temperature sensor" refers to a device that detects or measures the degree or intensity of heat present in a substance, object, or fluid.

A "therapy solution reservoir" refers to any container or reservoir that holds a physiological compatible fluid.

The term "total bicarbonate buffer concentration" refers to the total concentration of bicarbonate ($HCO_3^-$) ion and a conjugate acid of bicarbonate in a solution or composition.

A "therapy solution reservoir" refers to any container or reservoir that holds a physiological compatible fluid.

The terms "treating" and "treatment" refer to the management and care of a patient having a pathology or condition by administration of one or more therapy contemplated by the present invention. Treating also includes administering one or more methods of the present invention or using any of the systems, devices or compositions of the present invention in the treatment of a patient. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "uremic wastes" refers to a milieu of substances found in patients with end-stage renal disease, including urea, creatinine, beta-2-microglobulin.

The term "ultrafiltrate" refers to fluid that is removed from a subject by convection through a permeable membrane during hemodialysis, hemofiltration, hemodiafiltration, or peritoneal dialysis. The term "ultrafiltrate," as used herein, can also refer to the fluid in a reservoir that collects fluid volume removed from the patient, but such a reservoir may also include fluids or collections of fluids that do not originate from the subject.

The term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. During ultrafiltration, a "filtrate" or "ultrafiltrate" that passes through the filter medium is separated from a feed fluid. In general, when transport across a membrane is predominantly diffusive as a result of a concentration driving force, the process is described herein as dialysis. When transport is primarily convective as a result of bulk flow across the membrane induced by a pressure driving force, the process is ultrafiltration or hemofiltration depending on the need for substitution solution as the membrane passes small solutes but rejects macromolecules. The term "ultrafiltration" can also refer to the fluid removal from blood during a dialysis or a hemofiltration process. That is, ultrafiltration refers to the process of passing fluid through a selective membrane, such as a dialysis or hemofiltration membrane, in either a dialysis, a hemodiafiltration, or a filtration process.

The terms "unbuffered sodium bicarbonate" or "solution of unbuffered sodium bicarbonate" refer to a sodium bicarbonate composition that is not buffered with a conjugate acid or base in any amount, proportion or pH adjustment.

The term "upper position" and "lower position" are relative terms to each other wherein the upper position is at a higher elevation than the lower position.

The term "upstream" refers to a direction opposite to the direction of travel of a moving dialysate or other fluid within a conduit or flow path.

The term "Urea Reduction Ratio" or "URR" refers to a ratio defined by the formula below:

$$URR = \frac{U_{pre} - U_{post}}{U_{pre}} \times 100\%$$

Where:
$U_{pre}$ is the pre-dialysis urea level
$U_{post}$ is the post-dialysis urea level
Whereas the URR is formally defined as the urea reduction "ratio," in practice it is informally multiplied by 100% as shown in the formula above, and expressed as a percent.

The term "urea sensor" refers to a device for measuring or allowing for the calculation of urea content of a solution. The "urea sensor" can include devices measuring urease breakdown of urea and measurement of the resulting ammonium concentration. The sensing methods can be based on any one of conductimetric, potentiometric, thermometric, magnetoinductive, optical methods, combinations thereof and other methods known to those of skill in the art.

The term "vacuum" refers to an action that results from application of a pressure that is less than atmospheric pressure, or negative to the reference fluid or gas.

The term "vent" as referred to in relationship to a gas, refers to permitting the escape of a gas from a defined portion of the system, such as, for example, as would be found in the degassing module.

The term "void volume" refers to a specific volume that can be occupied by a fluid in a defined space such as a dialysate circuit of the invention including all components contained therein.

The terms "waste species," "waste products" and "impurity species" refers to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

The term "waste fluid" refers to any fluid that does not have a present use in the operation of the system. Non-limiting examples of waste fluids include ultrafiltrate, or fluid volume that has been removed from a subject undergoing a treatment, and fluids that are drained or flushed from a reservoir, conduit or component of the system.

The term "water feed" refers to a source of water that is added to a dialysate flow path by means of a pump or other delivery system.

The term "water source" refers to a source from which potable or unpotable water can be obtained.

The term "water source connection" or "water feed" refers to a state of fluid communication that enables water to be obtained from a water source and connected or feed into a receiving source or flow path.

The term "within" when used in reference to a sensor or electrode located "within" the sorbent cartridge refers to all, or part of the sensor or electrode is located inside, or encased by, at least part of the inner chamber formed from the sorbent cartridge wall.

The term "working dialysate solution" refers to a dialysate solution that is undergoing active circulation or movement through a system including conduits, pathways, dialyzers and cartridges.

Modular Dialysis System

The systems and methods for hemodialysis, hemofiltration, hemodiafiltration, and peritoneal dialysis of the present invention can have a dialysate regeneration system based on regenerative substances such as sorbent materials. Configurations of dialysate regeneration modules, or sorbent cartridges, are described that reduce the amount of certain regenerative substances, including sorbent materials in order to decrease the overall size and weight of the regeneration modules, for example, sorbent cartridges, to improve portability and reduce cost. The improved sorbent configurations are based in part upon the concept of reducing the concentration of certain species in the dialysate to increase the species removal rate or increase the capacity of certain regenerative substances to remove impurities, waste products and certain electrolytes from spent dialysate. For example, reducing the concentration of phosphate in dialysate generally increases the capacity of hydrous zirconium oxide for phosphate.

In any configuration, the improved sorbent configurations can also rely on the use of at least two regeneration modules, such as sorbent cartridges in series, where the first regeneration module can be loaded to full or total capacity and the second regeneration module can be loaded to breakthrough capacity, thereby increasing the utilization or efficiency of the regenerative substances. By increasing the utilization of a regenerative substance, such as hydrous zirconium oxide, less regenerative substance will be required, thereby decreasing the size and cost of the dialysate regeneration system. Breakthrough occurs when the outflow concentration of a particular species from a sorbent cartridge becomes non-zero. In general, after breakthrough the concentration of a particular species exiting a regeneration module will continue to increase until it equals the inlet concentration, at which point the regeneration substance will be loaded to full or total capacity. A second regeneration module can be placed after the first regeneration module to remove species that have exceeded the breakthrough and total capacity of the first regeneration module.

In any embodiment, a system for kidney replacement therapy and dialysate regeneration can have a dialysate circuit, or flow loop, for circulating a dialysate through a dialyzer, where at least one waste species enters the dialysate, and a dialysate regeneration unit for removing at least a portion of the waste species and releasing at least one conductive species to the dialysate or removing at least one conductive species from the dialysate and releasing at least one conductive species to the dialysate. A control, or ultrafiltration, pump optionally in fluid communication with an ultrafiltrate reservoir that can pump fluid into or out of the dialysate flow loop at a position downstream from the dialyzer and upstream from the dialysate regeneration unit. The dialysate flow loop can have a controlled compliant volume such that operation of the control pump in an efflux direction causes a net transfer or removal of fluid across the dialyzer membrane from the blood on the extracorporeal side of the membrane to the dialysate generating an ultrafiltrate. In any embodiment, the ultrafiltrate can be added to the ultrafiltrate reservoir. Conversely, operation of the control pump in an influx direction causes a net transfer or addition of fluid across the dialyzer membrane from the dialysate to the blood on the extracorporeal side of the membrane.

FIG. 1 is an example of an apparatus that includes a dialysis circuit, or flow loop, including a blood circuit or flow path 21 and a dialysate regeneration circuit or flow path 33 separated by a membrane 25 of a dialyzer 20. The blood enters the dialyzer 20 through a blood line inlet 22 and exits through a blood line outlet 24. The dialysate flow loop 33 shown in FIG. 1 is a controlled compliant flow loop.

The regenerated dialysate 36 is in fluid communication with a reconstitution system 43 downstream of the dialysate regeneration unit 34. The reconstitution system includes an infusate pump 42 and an infusate reservoir 44. The purpose of the reconstitution system 43 is to rebalance and ensure that the dialysate contains the appropriate amount of electrolytes and buffer. In various embodiments, the infusate reservoir 44 can include a single reservoir or multiple reservoirs each containing a different compound. For example, in some embodiments the infusate reservoir 44 can include a reservoir containing a concentrated electrolyte solution such as a solution including calcium acetate, magnesium acetate and potassium acetate. In other embodiments, the infusate reservoir 44 can include an additional reservoir containing a concentrated buffer solution, such as a solution including sodium bicarbonate. Further, it will be understood that any embodiment can include more than one reconstitution system 43.

Blood circulating through the dialyzer 20 via the flow path 21 can exchange waste components with the dialysate circulating through the dialyzer 20 and the dialysate flow loop 33. For example, waste species such as ions and uremic toxins, such as uric acid, creatinine, 1β-microglobin and urea, diffuse from the blood to the dialysate within the dialyzer 20 via the 25, which is often semi-permeable As such, without ongoing removal of waste species from the dialysate to maintain a concentration gradient of waste species between the blood and the dialysate in the dialysate flow loop 33, the concentration of the waste species in the dialysate flow loop 33 will reach equilibrium with the content of waste species in the blood.

Regeneration of the dialysate in the dialysate flow loop 33 can be achieved by contacting the dialysate with sorbents contained within the dialysate regeneration unit 34. Examples of useful sorbent materials include the REDY sorbent system; U.S. Pat. Nos. 3,669,880, 3,989,622, 4,581,141, 4,460,555, 4,650,587, 3,850,835, 6,627,164, 6,818,196 and 7,566,432; U.S. Patent Publications 2010/007838, 2010/0084330, and 2010/0078381; and International Patent Publication WO 2009/157877 A1, which are incorporated herein by reference.

In some embodiments, the dialysate regeneration unit 34 can contain multiple materials selected from the group: 1) a urease-containing material, where urease is an enzyme that catalyzes the conversion of urea to ammonium ions and carbon dioxide; 2) a zirconium phosphate (ZrP) material that has the capacity to act as a cation exchanger by absorbing a large quantity of ammonium ions in exchange for sodium and hydrogen ions. The zirconium phosphate can also absorb ammonium ions in exchange for potassium ions; 3) a hydrous zirconium oxide material (ZrO), which acts as an anion exchanger by exchanging phosphate for acetate; 4) an activated carbon material that has a surface area for adsorption of a wide range of impurities, including metal ions and uremic toxins, such as uric acid, creatinine, and β2-microglobin; and 5) other ion-exchange materials for removing cations and anions Ion-exchange materials can include weak and strong acid cation exchange resins, weak and strong basic anion exchange resins, chelating ion exchange resins, or other ion exchange resins known to this skilled in the art. The term zirconium oxide is used interchangeably with the term hydrous zirconium oxide.

In any embodiment, the zirconium phosphate material can be replaced with a magnesium phosphate material. Further, in any embodiment the hydrous zirconium oxide material can be replaced with activated alumina.

The principal waste species removed during treatment of a patient is urea, which accumulates in the blood of individuals with various degrees of kidney disease or impairment. Since urea is an electrically neutral species, the dialysate regeneration unit 34 can convert urea to a charged ammonium species that can then be removed from the circulating dialysate. However, in order to maintain electrical neutrality, the removal of charged ammonium species must be complemented by exchange of the charged ammonium with another charged species, which is sodium ion in certain embodiments.

The regenerated dialysate 36 passes through the dialyzer 20 and exits as waste dialysate 26. The waste dialysate 26 flow passes an ultrafiltration unit or system 29, for example, including an ultrafiltration pump 28 and an ultrafiltration reservoir 30. The ultrafiltration pump 28 removes fluid from the dialysate flow loop 33, and because of the dialysate loop's fixed volume, fluid is drawn across the dialyzer membrane 25 from the blood. The ultrafiltrate system 29 acts to remove ultrafiltrate from the patient and remove any other fluid added into the dialysate loop 33, such as fluid from the reconstitution system 43. The fluid removed by the ultrafiltrate pump 28 can be collected in the ultrafiltrate reservoir 30.

In certain embodiments, the dialysate flow loop 33 has a controlled compliant volume. As such, fluid is in passive equilibrium and does not provide for net flow from the extracorporeal circuit to the dialysate flow loop 33 due to the controlled compliant volume of the dialysate loop 33. The net balance of fluid can be prevented from passively flowing between the flow loop 33 to the extracorporeal circuit via the dialyzer 20, since such a transfer of fluid would leave a vacuum in the flow loop 33 or require that the volume of the flow loop 33 be expanded. Since the dialyzer can be a high-flux type that readily allows for the passage of water, there can be some fluid flux, or backfiltration, back and forth across the dialyzer membrane 25 due to the pressure differential between the blood and dialysate sides of the membrane 25. However, this is a localized phenomenon due to the low pressure required to move solution across the membrane and does not result in any net fluid gain or loss by the patient.

As an example, in certain embodiments the dialysate flow loop 33 can have a void volume from about 0.15 L to about 0.5 L. As additional examples, other embodiments of the dialysate flow loop 33 can have a void volume from about 0.2 L to about 0.4 L, or from 0.2 L to about 0.35 L. Other volumes can be envisioned by those of ordinary skill in the art, depending on parameters such as patient weight, size, and health condition. The system can be designed as a portable system, as a desktop system or as a large system suitable for heavy usage in a clinical setting. Hence, both large volumes greater than 0.5 L to about 5 L, and micro-volumes from as small as 0.1 L to about 0.5 L, for example, 0.1 L to 0.2 L, 0.1 L to 0.3 L, 0.1 L to 0.4 L, 0.2 L to 0.3 L, 0.3 L to 0.4 L, or 0.3 L to 0.5 L are contemplated by the invention.

Figure 2:
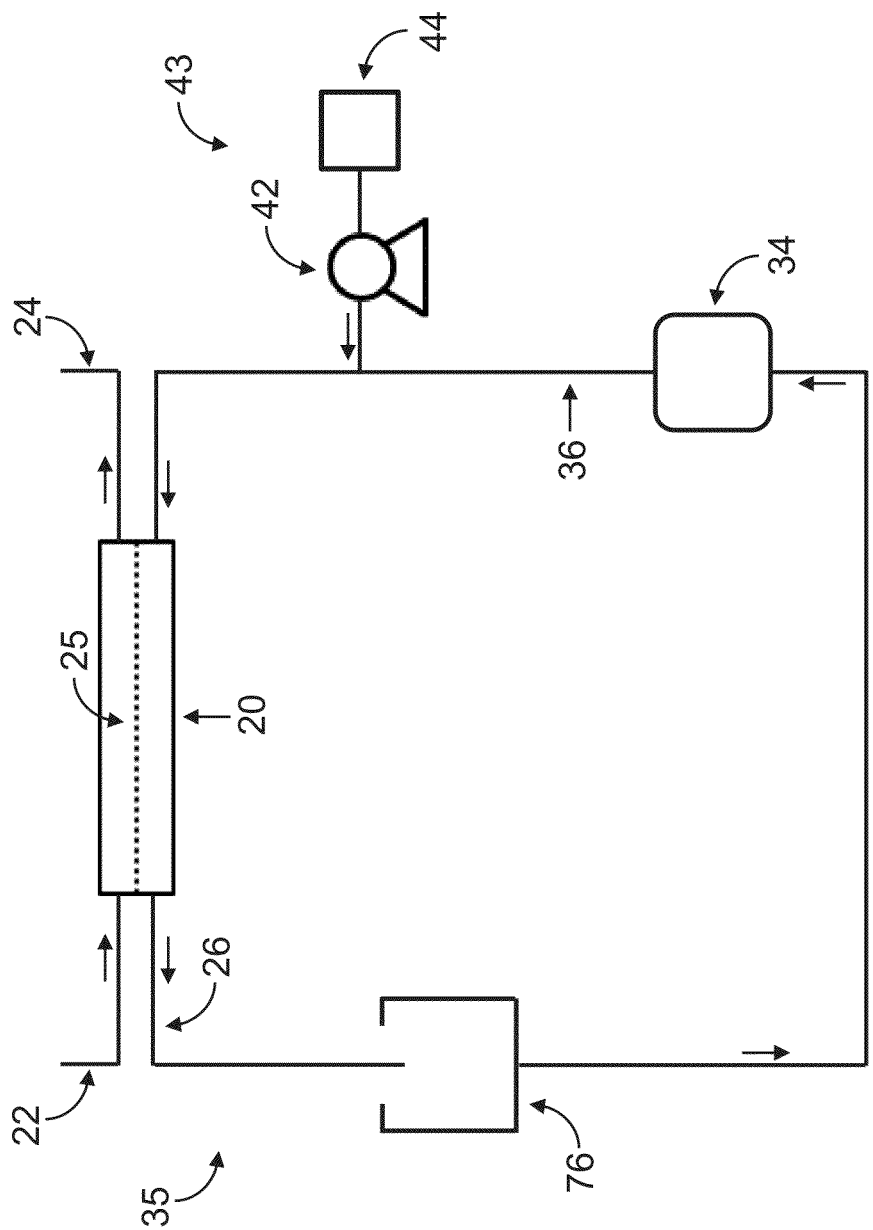
FIG. 2 is a flow diagram of a dialysate regeneration system associated with an open, non-fixed volume dialysate circuit.

FIG. 2 depicts a representative dialysis system similar to that shown in FIG. 1, except that the dialysate flow loop 35 includes a variable-volume dialysate reservoir 76 in place of the ultrafiltration system 29 of FIG. 1. Thus, the volume of dialysate fluid contained in the dialysate reservoir 76, and thus, the volume of the dialysate flow loop 35, can vary during the course of a hemodialysis therapy session. Specifically, the volume of dialysate fluid in the dialysate reservoir 76 can increase in proportion to the volume of ultrafiltrate removed from the patient by filtration across the dialyzer membrane 25. For use with the variable-volume reservoir 76 of FIG. 2, ultrafiltration may be controlled by any one of balance chambers and an ultrafiltration (UF) metering pump, duplex metering pumps and a UF metering pump, and transmembrane pressure regulators with mass or volume measurement (not shown). As used herein, the term ultrafiltrate can include fluid contained in the dialysate reservoir 76.

Figure 3:
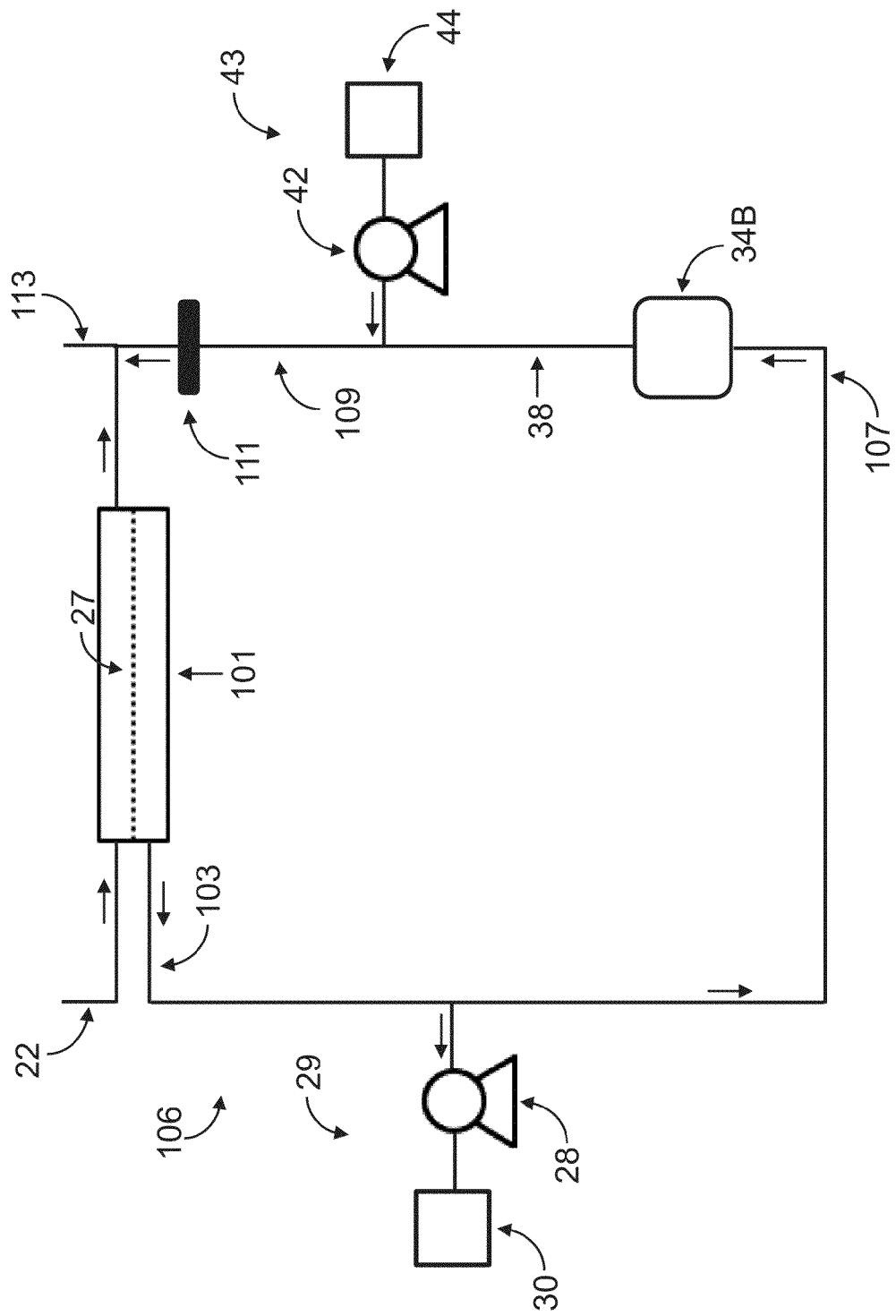
FIG. 3 is a flow diagram of a hemofiltration regeneration system associated with a controlled compliant filtrate circuit.

FIG. 3 shows a flow diagram for a representative hemofiltration system having a controlled compliant filtrate flow loop 106 utilizing a filtrate regeneration unit 34B. Hemofiltration can have certain benefits over hemodialysis, including higher convective clearance, which increases the clearance rate of middle molecular weight species like beta-2-microglobulin. As shown in FIG. 3, the blood can enter a hemofilter 101 by way of the blood line inlet 22 and a fluid can be filtered across at least one membrane 27 contained in the hemofilter 101. For example, the hemofilter 101 can include a hollow-fiber dialyzer, a plate-and-frame dialyzer, or any other suitable hemofilter. The hemofilter 101 can contain high-flux or low-flux membranes, for example, made of polysulfone, polyethersulfone, poly(methyl methacrylate), cellulose, modified-cellulose or any other suitable material. After exiting the hemofilter 101, the filtrate 103 is in fluid communication with an ultrafiltration pump 28, whereby fluid volume can be removed from the filtrate 103 and can be collected in the ultrafiltration reservoir 30.

The filtrate can then pass through a filtrate regeneration unit 34B and an infusate system 43 as described in FIG. 1. The regenerated filtrate 109 further can pass through a microbial filter 111 before being directly infused into the subject's bloodstream as replacement fluid. The microbial filter 111 may remove both viable organisms and endotoxin. The microbial filter may be a single filter, or multiple filters, including redundant filters. In various embodiments, the microbial filter 111 can include, for example, an ultrafilter, sterile filter, or any other suitable microbial filter. In any embodiment, the microbial filter 111 can include any material that is suitable for a hemofilter, for example, with pore sizes 0.2 microns or smaller.

In FIG. 3, an example of post-dilution hemofiltration is given. Those skilled in the art will recognize that pre-dilution hemofiltration can also be performed with this system if the replacement fluid is infused to the arterial line prior to the dialyzer blood inlet, rather than the venous line.

Figure 4:
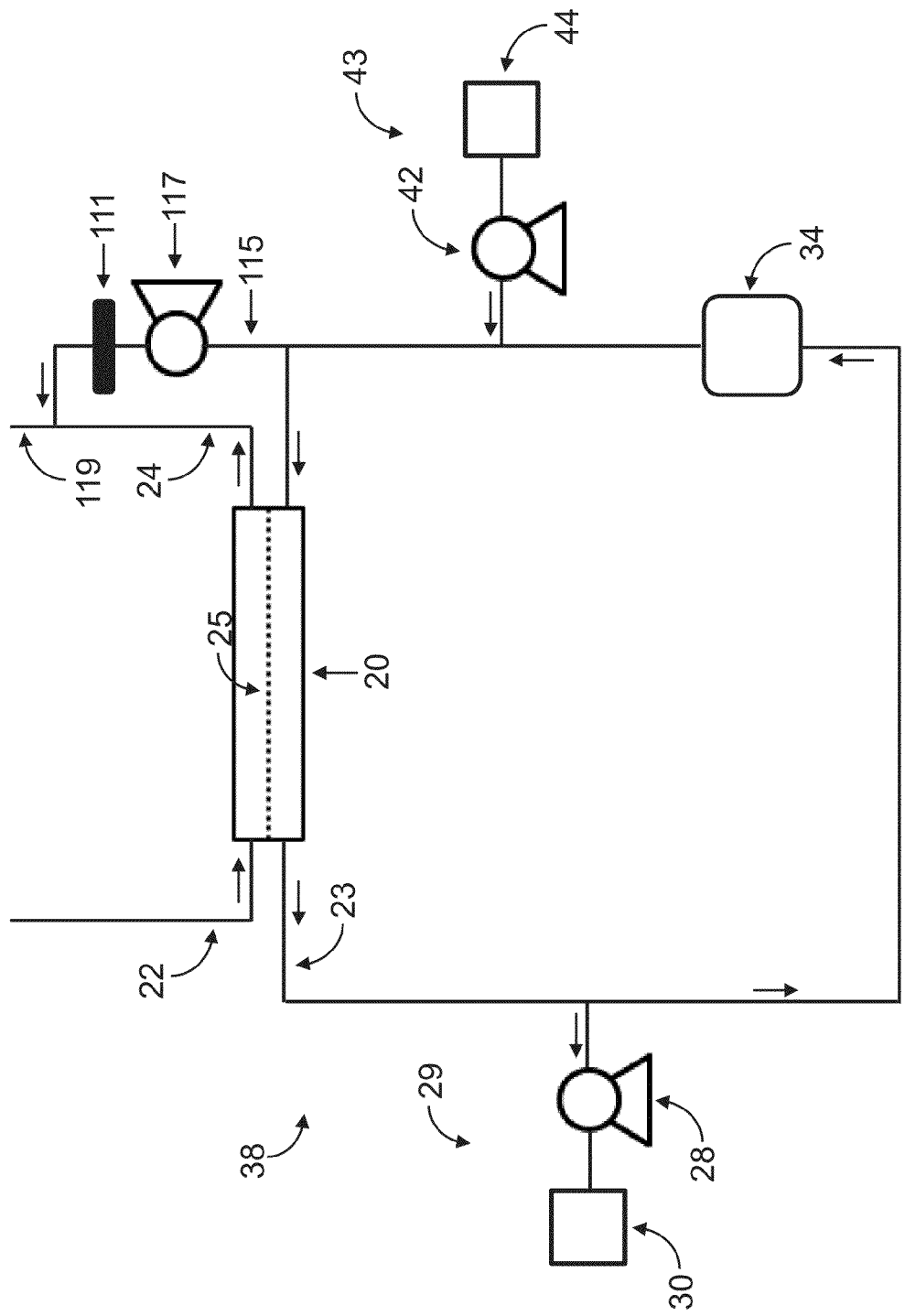
FIG. 4 is a flow diagram of a hemodiafiltration regeneration system associated with a controlled compliant dialysate circuit.

FIG. 4 shows a flow diagram of a representative hemodiafiltration system having a fixed-volume dialysate flow loop 38 utilizing a dialysate regeneration unit 34. Hemodiafiltration can combine the benefits achieved with both hemodialysis and hemofiltration, including maximum small molecule diffusive clearance and maximum middle molecule convective clearance. As shown in FIG. 4, the blood enters the dialyzer 20 by way of the arterial blood line 22 and a fluid can be filtered across the membrane 25 contained in the dialyzer 20. After exiting the dialyzer 20, the spent dialysate 23 is in fluid communication with an ultrafiltration pump 28, which can remove fluid volume from the spent dialysate 23. The removed fluid volume can be collected in the ultrafiltration reservoir 30. In any embodiment, the dialysate can be recirculated in the dialysate flow loop 38 with one or more pump contained in the dialysate regeneration unit 34. The dialysate can flow through the dialysate regeneration unit 34 and the infusate system 43 as described with reference to FIG. 1.

In any embodiment, a portion of the regenerated dialysate 115 can be diverted from the dialysate flow loop 38 by way of a replacement fluid pump 117 and be passed through a microbial filter 111 as described in FIG. 3. Then, the regenerated dialysate 115 can be added to the venous blood line 24 downstream from the dialyzer 20. The resulting mixture of post-dialyzer blood from the venous blood line 24 and regenerated dialysate 115 can be directly infused into the subject's blood as replacement fluid by way of the venous blood line 119.

In FIG. 4, an example of post-dilution hemodiafiltration is given. Those skilled in the art will recognize that pre-dilution hemodiafiltration can also be performed with this system if the regenerated dialysate, or replacement fluid 115 is infused to the arterial line prior to the dialyzer blood inlet, rather than the venous line.

Figure 5:
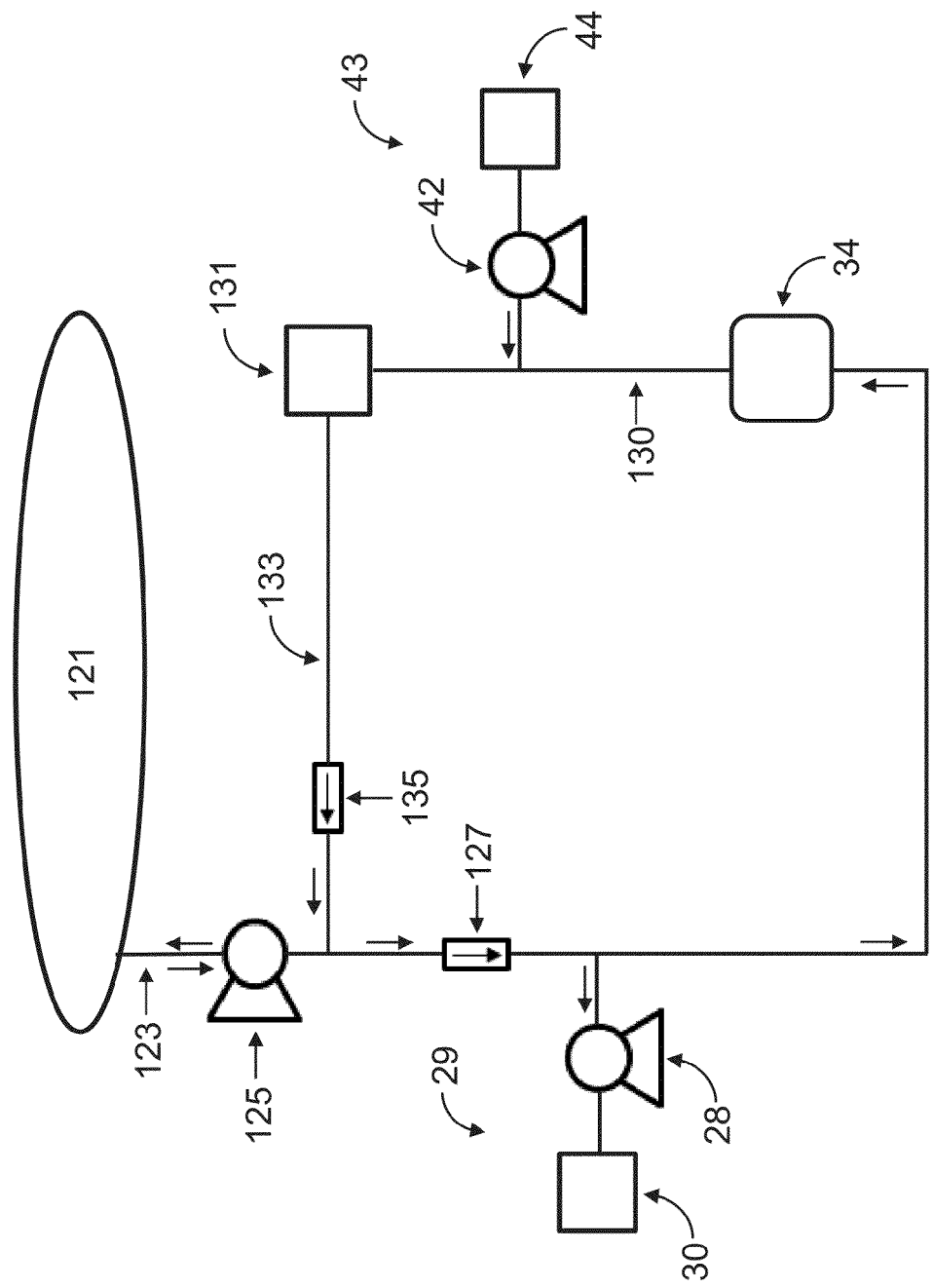
FIG. 5 is a flow diagram of a dialysate regeneration system associated with a peritoneal dialysis system.

FIG. 5 shows a flow diagram of a peritoneal dialysis system utilizing a dialysate regeneration unit 34. Initially, a patient's peritoneal cavity 121 can be filled with a volume of dialysate by way of a catheter 123. After a certain period of dwell time, spent dialysate is drawn out of the peritoneal cavity 121 through the catheter 123 using a reversible, or bi-directional, dialysate pump 125. The spent dialysate can flow through a check valve 127 and is prevented from flowing through flow line 133 by another check valve 135. Those skilled in the art will recognize that other configurations of pumps and valves can accomplish the same function, for example, valves 127 and 135 can be combined into a single 3-way valve, or pump 125 may be non-reversible if valves 127 and 135 are 2-way valves and pump 125 is placed downstream from valve 127. The spent dialysate can flow through the dialysate regeneration unit 34 and communicate with the infusate system 43. In the case of peritoneal dialysis the infusate reservoir 44 can include an infusate solution containing a high concentration of glucose or icodextrin.

In any embodiment, the regenerated dialysate 130 can be collected in a dialysate reservoir 131 for temporary storage. After a desired amount of regenerated dialysate has been collected in the dialysate reservoir 131, the dialysate pump 125 can be reversed and fluid can be drawn out of the dialysate reservoir 131 through the check valve 135, and can be directed through the catheter 123 into the peritoneal cavity 121.

This process can be continued until the dialysate regeneration unit 34 has been exhausted or until the therapy session has been completed. At the end of a therapy session a certain volume of ultrafiltrate will have been added from the patient to the dialysate contained in the peritoneal cavity 121. The ultrafiltrate can be removed from the dialysate using the ultrafiltration pump 28 and collected in the ultrafiltration reservoir 30. In other words, during the therapy session, while spent dialysate is being removed from the patient, a portion of the spent dialysate can be removed as ultrafiltrate with the ultrafiltrate pump 28 and stored in the ultrafiltration reservoir 30. In general, the amount of ultrafiltrate generated by the subject during a therapy session varies depending on several factors, including individual peritoneum properties, dialysate composition, patient fluid volume, or overload. Therefore, care must be taken when operating the ultrafiltrate pump 28 during the therapy session in order to avoid depleting the dialysate contained in the peritoneal cavity 121.

Figure 6:
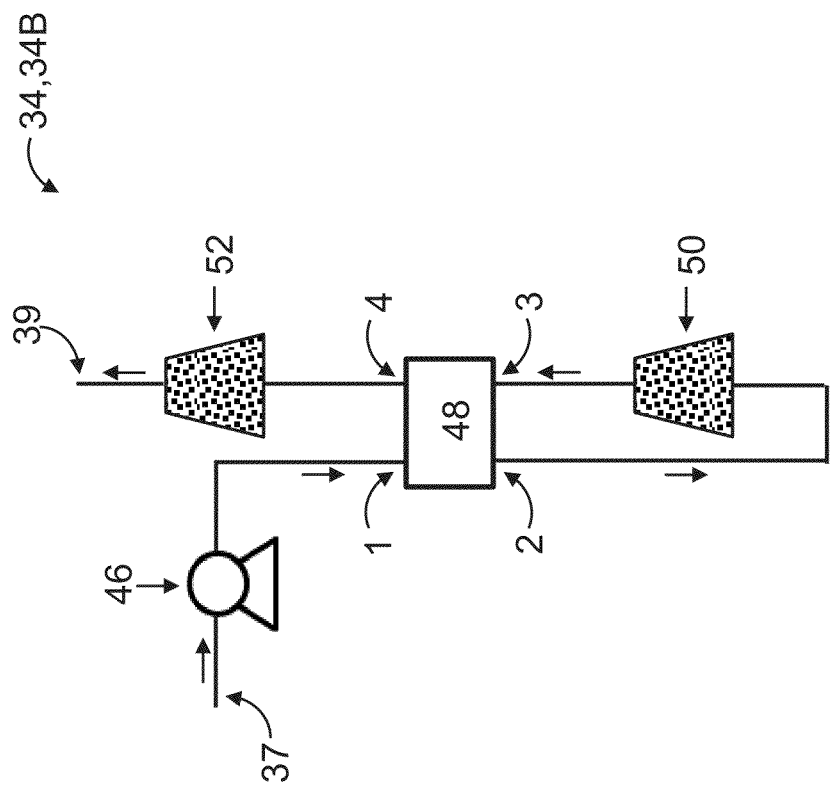
FIG. 6 is a flow diagram of a two-stage sorbent cartridge configuration including a single pump and a mixing chamber.

FIG. 6 shows a flow diagram of a representative two-stage regeneration unit, including a first sorbent cartridge 50 and a second sorbent cartridge 52, that can be used as the dialysate regeneration unit 34 in the embodiments of FIGS. 1, 2, 4 and 5 and the filtrate regeneration unit 34B in the embodiments of FIG. 3. Spent dialysate or filtrate 37 can be circulated through the dialysate or filtrate regeneration unit with a recirculation pump 46. The recirculation pump 46 also acts to recirculate dialysate around the dialysate flow loop 33 in FIG. 1, dialysate flow loop 35 in FIG. 2, filtrate flow loop 106 in FIG. 3 and dialysate flow loop 38 in FIG. 4. The dialysate or filtrate flows through a mixing chamber 48, also referred to as a proportioning chamber or a dilution chamber, entering through a first-pass inlet 1 and exiting through a first-pass outlet 2. The dialysate or filtrate then flows through a sorbent cartridge 50, re-enters the mixing chamber through a second-pass inlet 3, and exits the mixing chamber 48 through a second-pass outlet 4.

The mixing chamber 48 is designed to provide complete mixing between the dialysate or filtrate entering through the first-pass inlet 1 and the dialysate or filtrate entering through the second pass inlet 3. Ideally, the resulting dialysate or filtrate exiting the mixing chamber 48 through each the first-pass outlet 2 and the second-pass outlet 4 contains equal concentrations of all dialysate or filtrate components. In some embodiments, the mixing chamber 48 can contain static mixing elements to facilitate complete mixing of the dialysate or filtrate entering the mixing chamber 48 at the first-pass inlet stream 1 and the second-pass inlet stream 3. In any embodiment, the mixing chamber 48 can contain one or more semi-permeable membranes separating the dialysate or filtrate stream entering the first-pass inlet 1 and exiting the first-pass outlet 2 from the dialysate or filtrate stream entering the second-pass inlet 3 and exiting the second-pass outlet stream 4. The semi-permeable membrane(s) can be sized appropriately to essentially achieve complete equilibration of the dialysate component concentrations in the dialysate or filtrate streams exiting the first-pass outlet stream 2 and the second-pass outlet stream 4.

The first sorbent cartridge 50 can contain regenerative substances that remove certain impurities or waste species from the spent dialysate or filtrate 37. In any embodiment the regenerative substances can include sorbent materials. For example, in certain embodiments the sorbent cartridge 50 can contain hydrous zirconium oxide for removing phosphate from the dialysate. Therefore, the dialysate or filtrate exiting the first sorbent cartridge 50 does not contain an appreciable amount of phosphate, and upon flowing in a second pass through the mixing chamber 48, entering by way of the second-pass inlet 3, will dilute the phosphate concentration of the dialysate or filtrate flowing in a first-pass through the mixing chamber 48, entering by way of the first-pass inlet 1.

The mixing, or proportioning, or dilution, of the mixing chamber 48 results in a relatively dilute dialysate or filtrate phosphate concentration, with respect to that entering first-pass inlet 1, exiting the mixing chamber through the first-pass outlet 2 and entering the first sorbent cartridge 50. For example, if the dialysate or filtrate enters the mixing chamber 48 through the first-pass inlet 1 with a phosphate concentration of 2 millimoles per liter, and the first sorbent cartridge 50 contains hydrous zirconium oxide resulting in complete removal of the phosphate, then the dialysate or filtrate streams will exit the first-pass outlet stream 2 and the second-pass outlet stream 4 with a phosphate concentration of 1 millimoles per liter, assuming complete mixing in the mixing chamber 48. This can be advantageous, because the dilution of certain species in the dialysate or filtrate can increase the removal capacity of certain sorbent materials. For example, hydrous zirconium oxide has a higher capacity for phosphate removal at lower phosphate concentrations.

Another advantage of the dialysate or filtrate regeneration unit of FIG. 6 is the ability to utilize the total capacity of the first sorbent cartridge 50. In a dialysate or filtrate regeneration unit having a single sorbent cartridge, the sorbent materials are typically used until breakthrough occurs. In some embodiments, the breakthrough concentration preferably should be less than 10 percent of the concentration in the dialysate or filtrate entering the sorbent cartridge. However, percentages greater than 10 percent such as 15, 17, 18, 20, 22, 25, 27, 33, 36, 45, 50, 55, 64, 75, 77, 81, 85, 90, and up to less than 100 percent are contemplated by the invention.

In particular, the first sorbent cartridge 50 of the two-stage dialysate or filtrate regeneration unit of FIG. 6 can be operated beyond breakthrough capacity, because the second sorbent cartridge 52 can be used to remove any impurities or waste species that pass through the first sorbent cartridge 50. Therefore, the first sorbent cartridge 50 can be operated until full or total capacity is reached. In some embodiments, the total capacity of the sorbent cartridge 50 can be substantially higher than its breakthrough capacity, depending on the properties of the sorbent materials. The increased efficiency of the dialysate or filtrate regeneration unit corresponding to the higher operating capacity of the sorbent cartridge can result in a reduction in the amount of total sorbent materials required for the dialysate or filtrate regeneration unit 34 or 34B, respectively.

Figure 7:
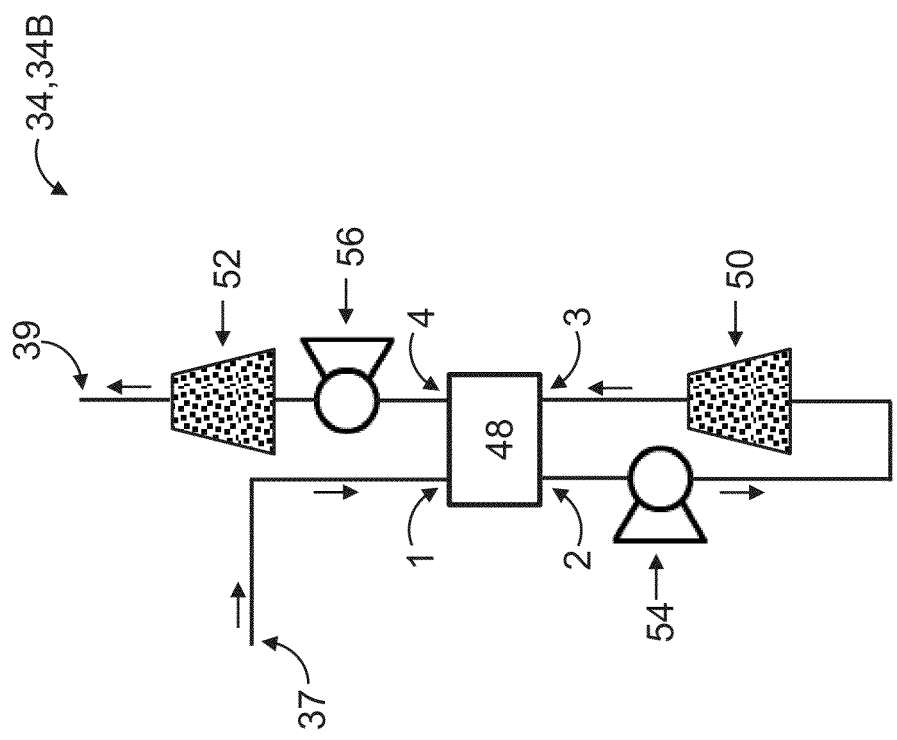
FIG. 7 is a flow diagram of a two-stage sorbent cartridge configuration including two pumps and a mixing chamber.

FIG. 7 is a flow diagram of an alternate embodiment of a two-stage regeneration unit that can be used as the dialysate regeneration unit 34 in the embodiments of FIGS. 1, 2, 4 and 5 and the filtrate regeneration unit 34B in the embodiments of FIG. 3. The dialysate or filtrate regeneration unit of FIG. 7 is similar to that of FIG. 6, except that the dialysate or filtrate regeneration unit of FIG. 7 includes two pumps 54, 56 for controlling the flow into and out of the mixing chamber 48. The two-pump configuration ensures substantially equal flow is achieved through each of the two sorbent cartridges 50, 52. The first pump 54 draws dialysate or filtrate out of the mixing chamber 48 via the first-pass outlet 2 and directs the dialysate or filtrate toward the first sorbent cartridge 50, from which the dialysate or filtrate goes back into the mixing chamber through the second-pass inlet 3. The second pump 56 draws dialysate or filtrate out of the mixing chamber 48 via the second-pass outlet 4 and directs the dialysate or filtrate toward the second sorbent cartridge 52.

Figure 8:
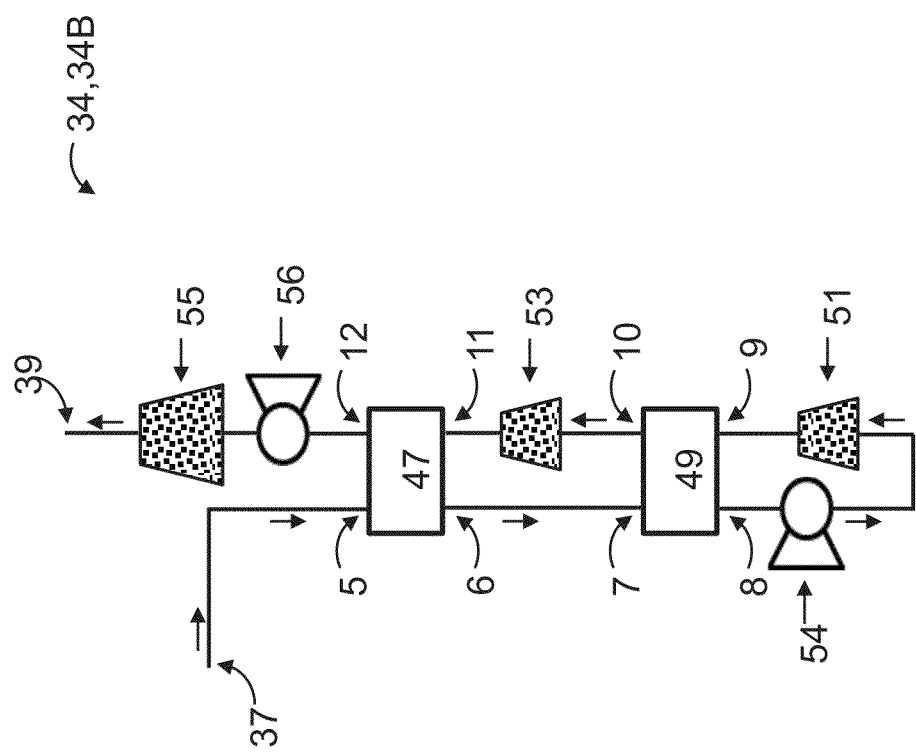
FIG. 8 is a flow diagram of a three-stage sorbent cartridge configuration including two pumps and two mixing chambers.

FIG. 8 is a flow diagram of a three-stage regeneration unit that can be used as the dialysate regeneration unit 34 in the embodiments of FIGS. 1, 2, 4 and 5 and the filtrate regeneration unit 34B in the embodiments of FIG. 3. The dialysate or filtrate regeneration unit of FIG. 8 is similar to that of FIG. 7, except that the dialysate or filtrate regeneration unit of FIG. 8 includes two mixing chambers 47, 49 and three sorbent cartridges 51, 53, 55. The additional mixing chamber 49 and sorbent cartridge 51 allow additional dilution of certain components of the dialysate or filtrate stream to occur. The additional dilution can improve the performance of the regenerative substances in terms of capacity. Assuming complete mixing in the mixing chambers 47 and 49 and equal flow into and out of each sorbent cartridge 51, 53 and 55, the concentration of certain components of the spent dialysate or filtrate 37 entering the dialysate or filtrate regeneration unit can be reduced by a factor of four in the dialysate or filtrate streams 8 and 10 exiting mixing chamber 49 and passing through sorbent cartridges 51 and 53. The placement of recirculating pumps 54 and 56 ensures equal flow of dialysate or filtrate into and out of each mixing chamber 47 and 49 and sorbent cartridge 51, 53, and 55.

The species in the dialysate or filtrate to be diluted are those species that are removed by the first two sorbent cartridges 51, 53. For example, in an embodiment the spent dialysate or filtrate 37 entering the dialysate or filtrate regeneration unit can have a phosphate concentration of 2 millimoles per liter, and the first and second sorbent cartridges 51, 53 can contain hydrous zirconium oxide, which can essentially completely remove phosphate. In this example, the phosphate concentration of the dialysate or filtrate from the first-pass outlet 8 and the second-pass outlet 10 exiting the second mixing chamber 49 equals 0.5 millimoles per liter, and the phosphate concentration of the dialysate or filtrate from the second-pass outlet 12 of the first mixing chamber 47 equals 1.0 millimole per liter.

One of ordinary skill in the art will recognize that in order to achieve additional dilution of certain species in the dialysate or filtrate, it can be beneficial to add additional sorbent cartridges and mixing chambers, beyond the number shown in FIG. 8. In general, if complete mixing is achieved in each mixing chamber and a particular species is completely removed from the dialysate in each sorbent cartridge, then the ultimate, dilution factor will equal $2^N$, where N is equal to the number of stages, or mixing chambers. The ultimate dilution factor, $2^N$, is achieved at the final or $N^{th}$ stage.

Figure 9:
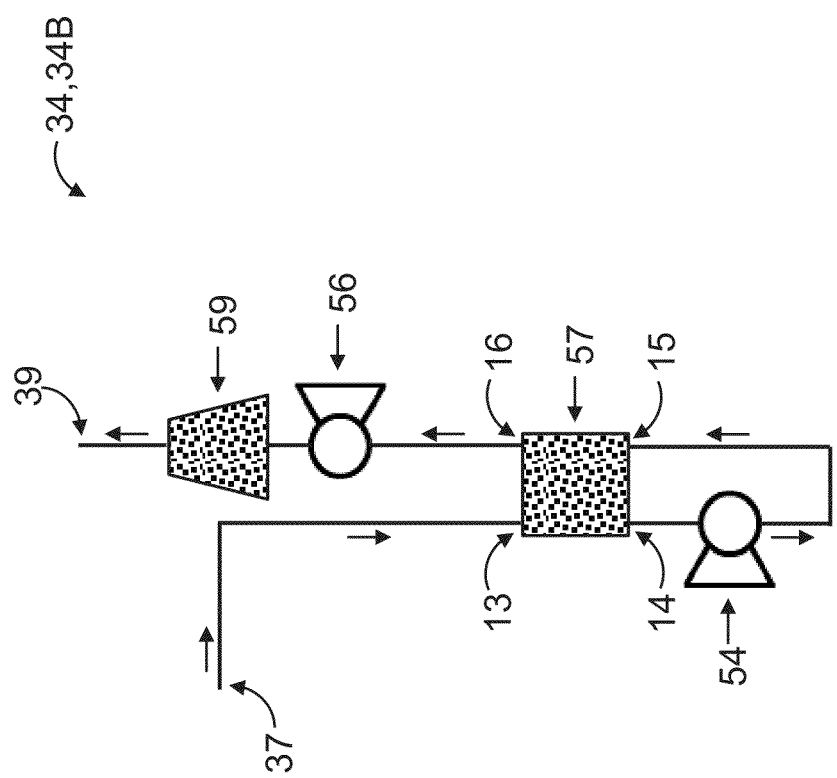
FIG. 9 is a flow diagram of a two-stage sorbent cartridge configuration including a counter-current sorbent cartridge, two pumps and a mixing chamber.

The flow diagram shown in FIG. 9 illustrates a dialysate or filtrate regeneration unit that can dilute the dialysate or filtrate without requiring multiple mixing chambers or sorbent cartridges. The spent dialysate or filtrate 37 enters a packed, counter-current sorbent cartridge 57 through the first-pass inlet 13 and is drawn out the first-pass outlet 14 with the first pump 54. In any embodiment, the counter-current sorbent cartridge 57 can be packed with sorbent materials of a particular size to promote mixing. In some embodiments, the sorbent cartridge 57 can further contain a static mixing element to promote mixing. For example, the static mixing element can take the form of fibrous membranes or filter paper placed across the cross-section (perpendicular to the general direction of flow) of the sorbent cartridge.

The dialysate or filtrate is then forced back into the sorbent cartridge 57 through the second-pass inlet 15 by the first pump 54 and exits the sorbent cartridge 57 through the second-pass outlet 16. As described with reference to FIG. 7, the second pump 56 draws dialysate out of the sorbent cartridge 57 through the second-pass outlet 16 in order to ensure equal flow entering and exiting the counter-current sorbent cartridge 57. The nature of a packed sorbent cartridge results in a tortuous path through which the first-pass inlet 13 and second-pass inlet 15 dialysate or filtrate streams must flow, resulting in good mixing between the streams.

Figure 10:
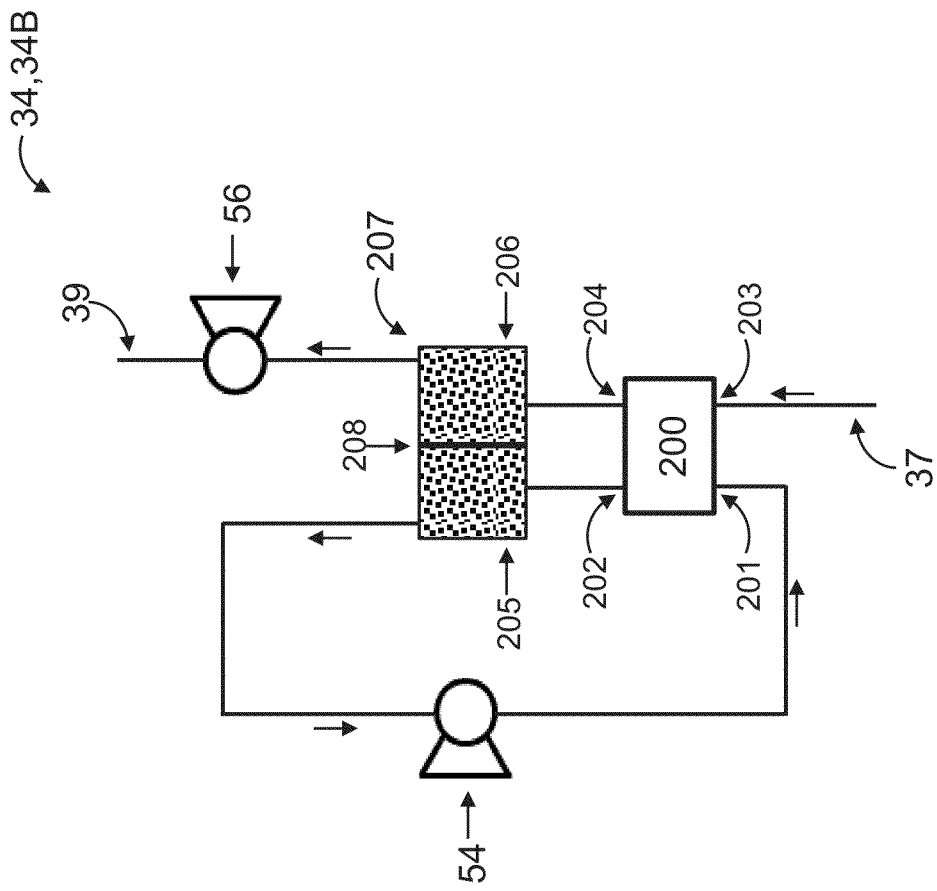
FIG. 10 is a flow diagram of a two-stage cartridge configuration contained in a single housing.

FIG. 10 is a flow diagram of an alternate embodiment of a two-stage regeneration unit that can be used as the dialysate regeneration unit 34 in the embodiments of FIGS. 1, 2, 4 and 5 and the filtrate regeneration unit 34B in the embodiments of FIG. 3. The dialysate or filtrate regeneration unit of FIG. 10 is similar to that of FIG. 7, except that a single sorbent cartridge housing is utilized containing an impermeable barrier 208 between a first sorbent compartment 205 and a second sorbent compartment 206. The two-pump configuration ensures substantially equal flow is achieved through each of the two sorbent compartments 205, 206. The first pump 54 draws dialysate or filtrate out of the mixing chamber 200 via the first-pass outlet 202 and directs the dialysate or filtrate toward the first sorbent compartment 205, from which the dialysate or filtrate goes back into the mixing chamber through the second-pass inlet 201. The second pump 56 draws dialysate or filtrate out of the mixing chamber 200 via the second-pass outlet 204 and directs the dialysate or filtrate toward the second sorbent compartment 206. The single sorbent cartridge housing minimizes the size of the system and potentially the cost of the sorbent cartridge.

EXAMPLES

Hydrous Zirconium Oxide Synthesis 170 grams of sodium hydroxide (Sigma-Aldrich, St. Louis Mo.) was dissolved in 500 milliliters (ml) of deionized water in a 1 liter flask and added to a 2 liter, 3-neck, round-bottom flask fitted with an overhead mixer and impeller. The mixer was operated at approximately 100 rpm, and 500 grams of zirconium-oxychloride-octahydrate (Inframat Advanced Materials, Manchester Conn.) was added to the flask over 3 minutes. Stirring was continued for an additional 10 minutes after addition of the zirconium-oxychloride-octahydrate. Then, the resulting slurry was poured through a Buchner funnel with 20 to 25 micron filter paper. The resulting filter cake was washed twice with 2.2 liters of deionized water. Next, the filter cake was transferred to a 4 liter flask, and 2 liters of deionized water and 60 ml of glacial acetic acid (Amresco, Solon Ohio) added.

The resulting slurry was mixed at approximately 100 rpm with an overhead mixer and impeller for 1 hour. Then, the slurry was poured through a Buchner funnel with 20 to 25 micron filter paper and washed twice with 2.2 liters of deionized water, or until the filtrate sodium concentration was less than 30 millimoles per liter of sodium. Next, the filter cake was allowed to air dry for several hours and then transferred to a glass dish for additional drying in a fume hood until a constant mass was achieved, which takes approximately 3 days. The resulting dry powder was added to a 106 micron sieve and stacked on top of a 45 micron sieve and collection pan. Then, the sieve stack was placed on a sieve shaker and agitated for about 3 hours. The fraction settled on the 45-micron sieve was collected in a jar and used as the hydrous zirconium oxide sorbent for phosphate removal. Typical yield of the 45- to 106-micron hydrous zirconium oxide was about 200 grams.

Hydrous Zirconium Oxide Column Testing 5 grams of hydrous zirconium oxide was packed into a 1 inch diameter Econo-Column (Bio-Rad, Hercules Calif.) with flow adapter (Bio-Rad, Hercules Calif.). The solution was pumped at approximately 12.3 milliliters per minute using a Masterflex peristaltic pump and silicone tubing. The solution passing through the column, the effluent, was collected and used to determine the average flow rate of each trial. The pumped solution consisted of: 110 millimolar (mM) sodium chloride (Sigma-Aldrich, St. Louis Mo.), 25 mM sodium bicarbonate (Sigma-Aldrich, St. Louis, Mo.), 2 mM sodium acetate (Sigma-Aldrich, St. Louis Mo.), and a varying concentration, between 0.7 mM or 2.6 mM, of sodium phosphate-monobasic-monohydrate (VWR, Radnor Pa.). The solution pH was brought close to 7.20 using hydrochloric acid (Sigma-Aldrich, St. Louis Mo.).

Figure 11:
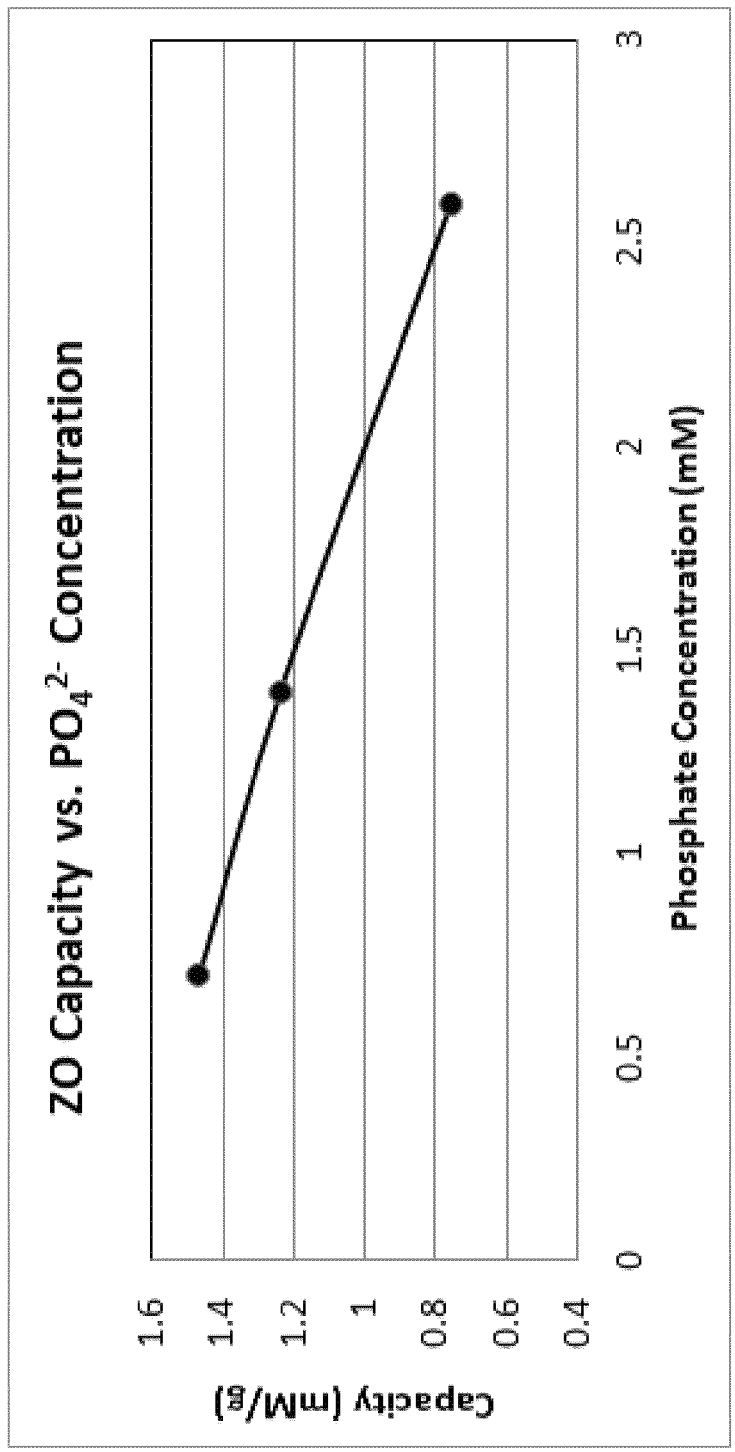
FIG. 11 is a graph depicting a representative relationship between the capacity of a hydrous zirconium oxide of a sorbent cartridge and the phosphate concentration of an associated dialysate solution.
Figure 15:
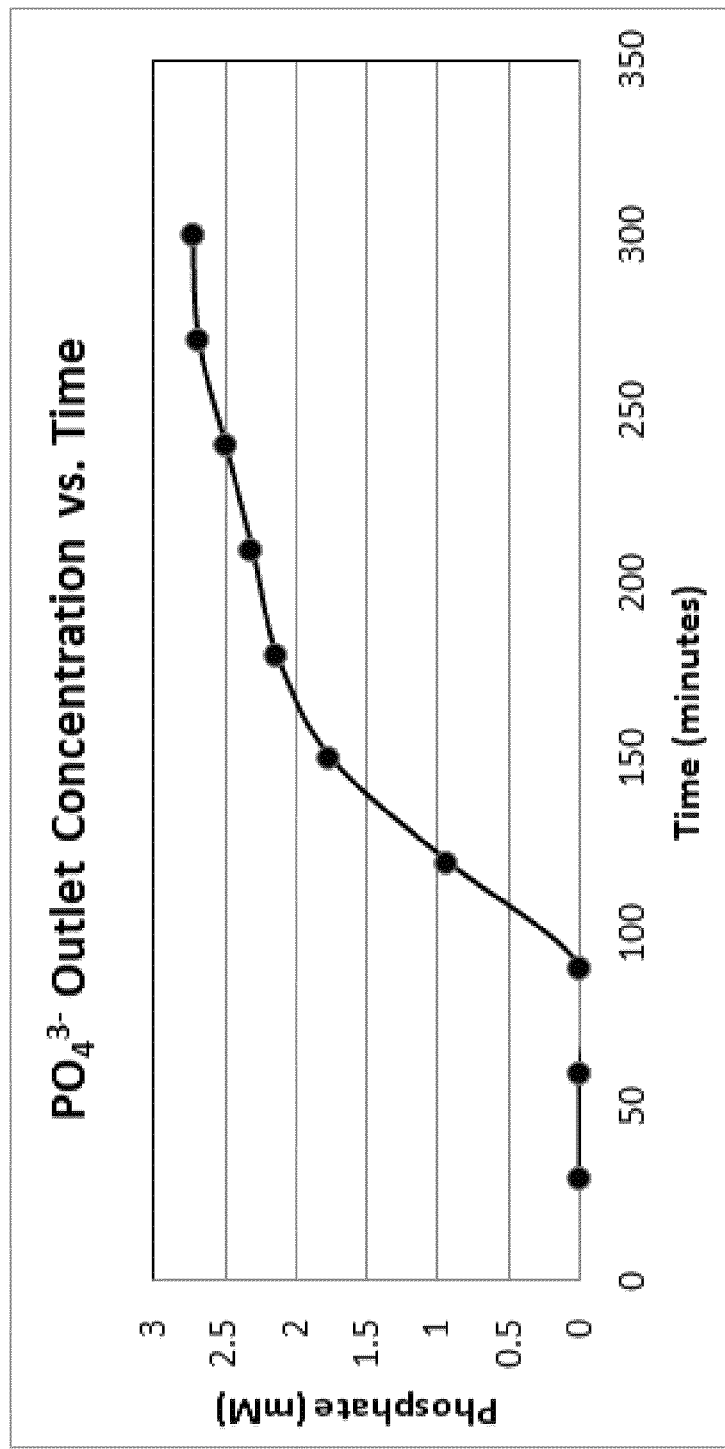
FIG. 15 is a graph depicting the effluent concentration of phosphate exiting a hydrous zirconium oxide sorbent cartridge.

Samples of the solution exiting the column, the effluent, were taken every 30 minutes in 2 ml microcentrifuge tubes (VWR, Radnor Pa.) and tested on a Bioprofile 300 (Nova Biomedical, Waltham Mass.) for phosphate concentration until an increase in phosphate concentration was seen in consecutive samples. The breakthrough capacity was calculated at the time point where the phosphate concentration first started to increase. As the concentration of phosphate in the starting solution increased, the capacity of hydrous zirconium oxide for phosphate decreased, as shown in FIG. 11. Therefore, a more dilute concentration of phosphate can maximize the efficiency of the hydrous zirconium oxide for phosphate removal. FIG. 15 is a graph depicting the effluent concentration of phosphate exiting the column for a 2.6 mM phosphate solution. The concentration profile from FIG. 15 was integrated to determine the breakthrough capacity and the total capacity. The breakthrough capacity was determined to be 0.7 mM of phosphate per gram of hydrous zirconium oxide. The total capacity was determined to be 1.1 mM of phosphate per gram of hydrous zirconium oxide. Therefore, only 64% of the total capacity was used until breakthrough occurred.

Zirconium Phosphate Column Testing

Sodium zirconium hydrogen phosphate (MEL Chemicals, Manchester, England), acid zirconium phosphate (MEL Chemicals, Manchester, England), and 100 micron silica beads (OPS Diagnostics, Lebanon N.J.) were mixed together in the ratio 17:3:6. The blend was added to a 1 inch diameter Econo-Column (Bio-Rad, Hercules Calif.) with flow adapter (Bio-Rad, Hercules Calif.) to allow about 3 hours of solution to be pumped without any ammonium break. Solution was pumped at approximately 12.3 ml per minute using a Masterflex peristaltic pump and silicone tubing. The solution passing through the column was collected and used to determine the average flow rate of each trial.

Three different solutions were pumped through the column, with constant concentrations of the following: 0.7 mM sodium phosphate-monobasic-monohydrate (VWR, Radnor Pa.), 0.4 mM creatinine (Sigma-Aldrich, St. Louis Mo.), 3 mM potassium chloride (Sigma-Aldrich, St. Louis Mo.), 1.5 mM calcium acetate hydrate (Sigma-Aldrich, St. Louis Mo.)

and 0.5 mM magnesium acetate tetrahydrate (Sigma-Aldrich, St. Louis Mo.). The concentrations of ammonium carbonate (Sigma-Aldrich, St. Louis Mo.), sodium chloride (Sigma-Aldrich, St. Louis Mo.) and sodium bicarbonate (Sigma-Aldrich, St. Louis Mo.) all varied as follows (in mM): 4, 123.3 and 16, respectively, for the first trial; 14, 133.3 and 6, respectively, for the second trial; and 19, 138.3 and 1, respectively, for the third trial. The pH of the solutions was brought to 7.0 using hydrochloric acid (Sigma-Aldrich, St. Louis Mo.).

Figure 12:
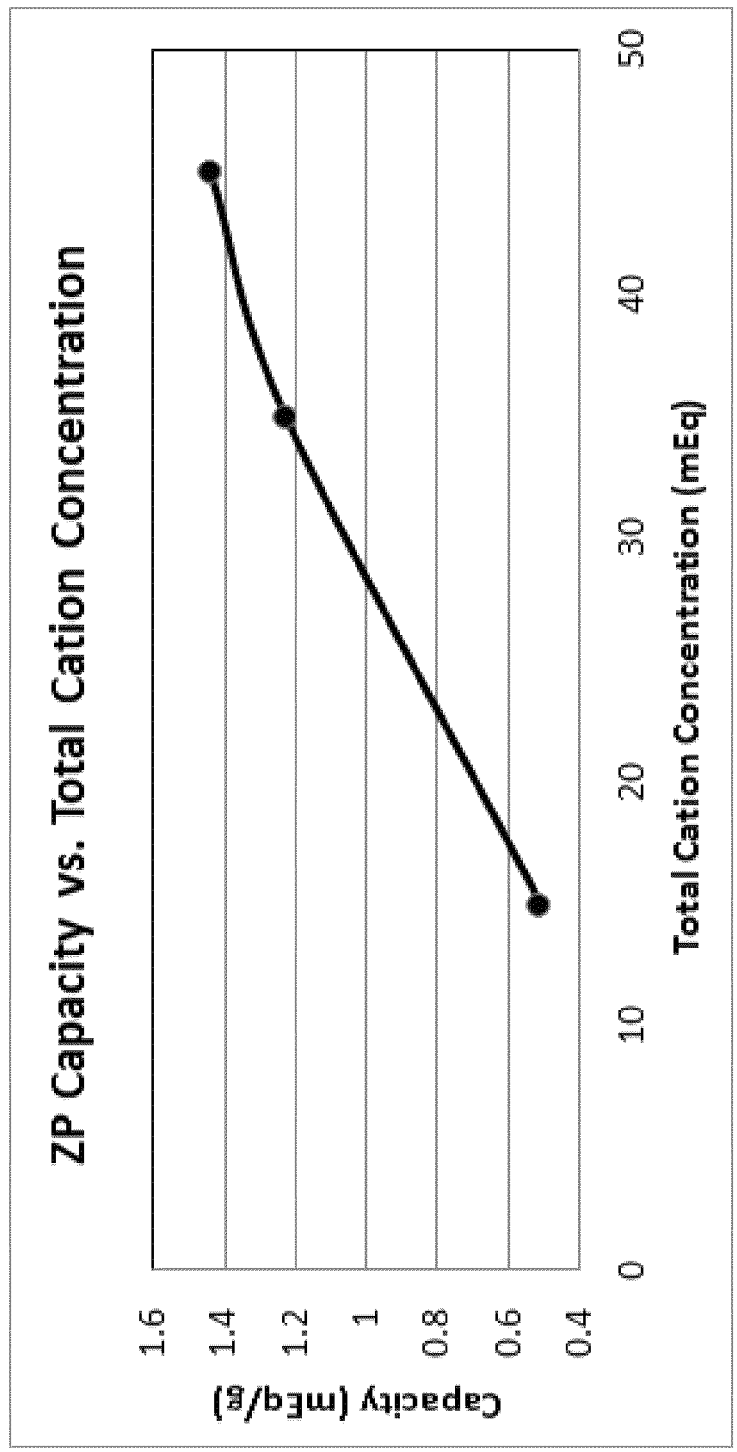
FIG. 12 is a graph depicting a representative relationship between the capacity of a zirconium phosphate with respect to the total cation concentration of an associated dialysate solution.

Samples were taken every 30 minutes in 2 ml microcentrifuge tubes (VWR, Radnor Pa.) and tested on a Bioprofile 300 (Nova Biomedical, Waltham Mass.) for ammonium concentration as well as a Critical Care Xpress (Nova Biomedical, Waltham Mass.) for calcium, magnesium and potassium concentration until an increase in cation concentration was seen in consecutive samples. The breakthrough capacity was calculated at the time point where the total cation concentration first started to increase. As the concentration of ammonium in the testing solution decreased, the millimolar equivalent capacity of the zirconium phosphate blend for cations in solution also decreased, as shown in FIG. 12. Thus, a solution with higher ammonium or urea concentration can maximize the zirconium phosphate blend capacity for the cations of interest.

2-Stage Sorbent Cartridge with Mixing Chamber

Figure 13:
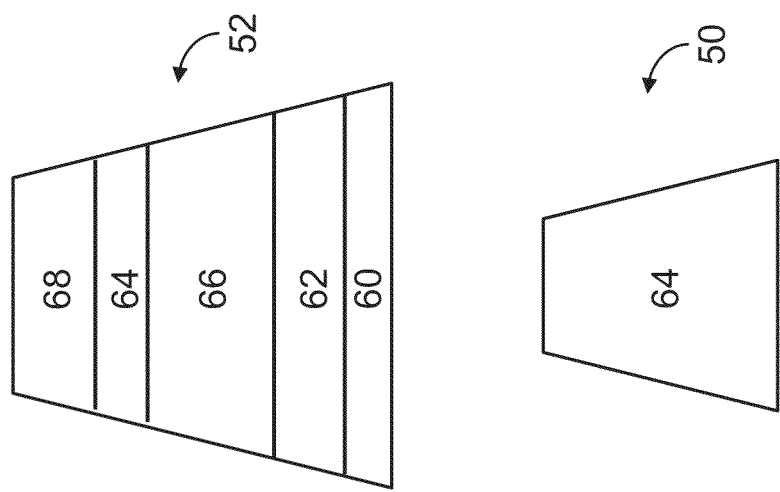
FIG. 13 illustrates a representative sorbent cartridge configuration.

A representative two-stage sorbent cartridge configuration that can be used with the dialysate or filtrate regeneration units of FIGS. 6 and 7 is shown in FIG. 13. As an example, with reference to FIGS. 6, 7 and 13, the spent dialysate or filtrate 37 entering the dialysate or filtrate regeneration unit can have the composition shown in Table 1 below.

TABLE 1

| Spent Dialysate Composition | |
|---|---|
| Component | Concentration (millimoles per liter) |
| Na$^+$ | 140 |
| K$^+$ | 5 |
| Ca$^{2+}$ | 1.5 |
| Mg$^{2+}$ | 0.5 |
| Urea | 20 |
| Phosphate, PO$_4^{3-}$ | 2 |
| Cl$^-$ | 120 |
| HCO$_3^-$ | 25 |
| Creatinine | 1 |
| pH (adjusted with HCl) | 7.2 |

Figure 14:
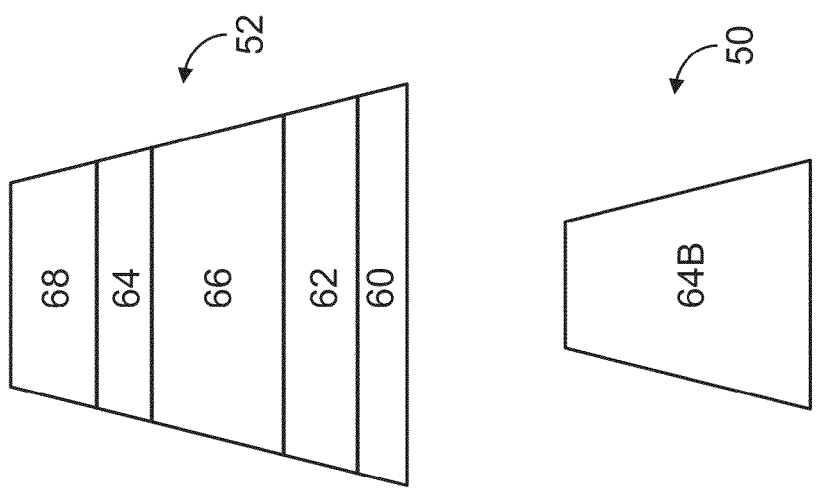
FIG. 14 illustrates another representative sorbent cartridge configuration.

In this example, the first sorbent cartridge 50 of FIG. 13 contains hydrous zirconium oxide 64 to remove phosphate from the dialysate or filtrate stream. Therefore, the first-pass outlet 2 and second-pass outlet 4 dialysate or filtrate streams exiting the mixing chamber 48 can have a phosphate concentration of 1 millimole per liter. Assuming a dialysate or filtrate flow rate of 0.4 liters per minute and a therapy time of 240 minutes, the amount of hydrous zirconium oxide 64 required in each of the sorbent cartridges 50, 52 can be 70 grams, based on a hydrous zirconium oxide capacity of 1.38 mM/g as shown in FIG. 11. In contrast, a single sorbent cartridge would require 192 grams of hydrous zirconium oxide based on a capacity of 1 mM/g for a 2 mM phosphate solution as shown in FIG. 11. Thus, 27 percent less hydrous zirconium oxide is required for the 2-stage sorbent cartridge system shown in FIG. 6 versus a single stage sorbent cartridge. Another example of a representative two-stage sorbent cartridge configuration that can be used with the dialysate or filtrate regeneration units of FIGS. 6 and 7 is shown in FIG. 14. This example illustrates the concept of using the first sorbent cartridge until total capacity is reached. As an example, with reference to FIGS. 6, 7 and 14, the spent dialysate or filtrate 37 entering the dialysate or filtrate regeneration unit can have the composition shown in Table 1 above. In this example, the first sorbent cartridge 50 of FIG. 14 contains hydrous zirconium oxide 64B to remove phosphate from the dialysate or filtrate stream. Therefore, the first-pass outlet 2 and second-pass outlet 4 dialysate or filtrate streams exiting the mixing chamber 48 can have a phosphate concentration of 1 millimole per liter. Assuming a dialysate or filtrate flow rate of 0.4 liters per minute and a therapy time of 240 minutes, the amount of hydrous zirconium oxide 64B required in sorbent cartridge 50, shown in FIG. 14 can be 45 grams, based on a hydrous zirconium oxide total capacity of 2.16 mM/g as shown in FIGS. 11 and 15. The amount of hydrous zirconium oxide 64 required in sorbent cartridge 52, shown in FIG. 14 will remain 70 grams, as described above. Therefore, by operating the hydrous zirconium oxide 64B to total capacity the total amount of hydrous zirconium oxide required can be 115 grams compared to 140 grams required for a 2-stage sorbent cartridge system where the hydrous zirconium oxide is run only to breakthrough capacity. In the above examples the second sorbent cartridge 52, shown in FIGS. 13 and 14, contains materials to remove the remaining species in the spent dialysate or filtrate, including alumina and urease 60, alumina 62, zirconium phosphate 66, hydrous zirconium oxide 64 and activated carbon 68. Since only phosphate is removed with the first sorbent cartridge 50, the other species present in the dialysate or filtrate do not change in concentration upon passing through the mixing chamber 48. Thus, the amount of each sorbent material required in the second sorbent cartridge 52, with the exception of hydrous zirconium oxide 64, is equivalent to the amount required in a single sorbent cartridge system. Because zirconium phosphate capacity for cations decreases with decreasing cation concentration, as shown in FIG. 12, it would not be beneficial to have zirconium phosphate in the first sorbent cartridge 50.

It will be apparent to one skilled in the art that various combinations and/or modifications and variations can be made in the dialysis system depending upon the specific needs for operation. Moreover, features illustrated or described as being part of one embodiment may be used on another embodiment to yield a still further embodiment.

The invention claimed is:

1. A regeneration system, comprising:
   a first regeneration module containing a first chosen regenerative substance;
   a second regeneration module containing the first chosen regenerative substance; and
   a first mixing chamber, wherein a first outlet stream of a fluid sequentially exits the first mixing chamber, flows through the first regeneration module in fluid communication with the first chosen regenerative substance and returns to the first mixing chamber, and a second outlet stream of the fluid sequentially exits the first mixing chamber and flows through the second regeneration module in fluid communication with the first chosen regenerative substance.

2. The regeneration system of claim 1, wherein a first inlet stream of the fluid that enters the first mixing chamber is mixed in the first mixing chamber with a second inlet stream of the fluid that enters the first mixing chamber.

3. The regeneration system of claim 2, wherein the first mixing chamber further comprises a static mixer element.

4. The regeneration system of claim 2, wherein the mixing chamber further comprises a semi-permeable membrane that separates the first inlet stream from the second inlet stream, and a solute diffuses from the first inlet stream to the second inlet stream.

5. The regeneration system of claim 2, wherein the second inlet stream includes at least a portion of the first outlet stream returning to the first mixing chamber.

6. The regeneration system of claim 2, wherein the first outlet stream and the second outlet stream have substantially the same component concentrations.

7. The regeneration system of claim 1, wherein the first regeneration module operates at a total capacity of the first chosen regenerative substance.

8. The regeneration system of claim 1, wherein the fluid comprises a dialysate solution, and the first chosen regenerative substance removes a waste species from the dialysate solution.

9. The regeneration system of claim 1, wherein the fluid comprises a filtrate solution, and the first chosen regenerative substance removes a waste species from the filtrate solution.

10. The regeneration system of claim 1, wherein the first chosen regenerative substance comprises at least one of urease, alumina, zirconium phosphate, zirconium oxide, or activated carbon.

11. The regeneration system of claim 1, wherein the second regeneration module further contains a second chosen regenerative substance, the first chosen regenerative substance removes a first waste species from the fluid, and the second chosen regenerative substance removes a second waste species from the fluid.

12. The regeneration system of claim 11, wherein the first chosen regenerative substance comprises at least one of urease, alumina, zirconium phosphate, zirconium oxide, and activated carbon, and the second chosen regenerative substance comprises at least one of urease, alumina, zirconium phosphate, zirconium oxide, and activated carbon.

13. The regeneration system of claim 11, wherein the first chosen regenerative substance comprises at least one of urease, alumina, zirconium oxide, and activated carbon, the second chosen regenerative substance comprises zirconium phosphate.

14. The regeneration system of claim 13, wherein the first chosen regenerative substance comprises zirconium oxide and the second regenerative substance comprises urease, alumina, zirconium oxide, zirconium phosphate and activated carbon.

15. The regeneration system of claim 1, further comprising:
a third regeneration module containing the first chosen regenerative substance; and
a second mixing chamber, wherein a third outlet stream of the fluid exits the second mixing chamber and flows through the first mixing chamber, a fourth outlet stream of the fluid exits the second mixing chamber and flows through the third regeneration module, a third inlet stream of the fluid enters the second mixing chamber, the fourth inlet stream enters the second mixing chamber, the first inlet stream consists of the third outlet stream, and the fourth inlet stream consists of the second outlet stream.

16. The regeneration system of claim 15, further comprising a first pump that operates to cause the fluid to flow through the first mixing chamber.

17. The regeneration system of claim 16, further comprising a second pump between the first mixing chamber and the second regeneration module that operates to cause the second outlet stream to flow.

18. A regeneration system, comprising:
a regeneration module containing a regenerative substance; and
a mixing chamber containing the regenerative substance, wherein a first stream of a fluid enters the mixing chamber in fluid communication with the regenerative substance, a second stream of the fluid exits and reenters the mixing chamber, and a third stream of the fluid exits the mixing chamber and flows through the regeneration module in fluid communication with the regenerative substance.

19. The regeneration system of claim 18, wherein the first stream is mixed in the mixing chamber with the second stream reentering the mixing chamber.

20. The regeneration system of claim 18, wherein the second stream and the third stream exiting the mixing chamber have substantially the same concentration of at least one component of the fluid.

21. The regeneration system of claim 18, wherein the fluid comprises a dialysate solution, and the regenerative substance removes a waste species from the dialysate solution.

22. The regeneration system of claim 18, wherein the fluid comprises a filtrate solution, and the regenerative substance removes a waste species from the filtrate solution.

23. The regeneration system of claim 18, wherein the regenerative substance comprises at least one of urease, alumina, zirconium phosphate, zirconium oxide, and activated carbon.

24. A dialysis system, comprising:
a dialyzer that facilitates transfer of a solute from blood to a dialysate;
a first regeneration module containing a first chosen regenerative substance;
a second regeneration module containing the first chosen regenerative substance; and
a first mixing chamber, wherein a first outlet stream of the dialysate sequentially exits the first mixing chamber, flows through the first regeneration module in fluid communication with the regenerative substance and returns to the first mixing chamber, and a second outlet stream of the dialysate sequentially exits the first mixing chamber, flows through the second regeneration module in fluid communication with the regenerative substance and flows through the dialyzer.

25. The dialysis system of claim 24, further comprising a dialysate flow path that allows fluid communication between the dialyzer, the first and second regeneration modules and the first mixing chamber, wherein the dialysate flow path, the dialyzer, the first and second regeneration modules and the first mixing chamber have a substantially fixed volume.

26. The dialysis system of claim 24, further comprising a dialysate flow path that is controlled compliant.

27. The dialysis system of claim 24, wherein the dialysis system is capable of selectively metering fluid into and out of the dialysate flow path.

28. The dialysis system of claim 27, wherein the dialysis system is capable of selectively metering fluid into and out of the dialysate flow path using any one of a control pump, a water pump, a salination pump, an acid concentrate pump, a replacement fluid pump, and combinations thereof.

29. The dialysis system of claim 24, wherein the dialysis system is capable of moving fluid bi-directionally in any one of the dialyzer, the first and second regeneration modules, the first mixing chamber, the dialysate flow path, the dialyzer, the first and second regeneration modules and the first mixing chamber.

30. The dialysis system of claim 24, further comprising a variable-volume dialysate flow path that allows fluid communication between the dialyzer, the first and second regeneration modules and the first mixing chamber.

31. The dialysis system of claim 30, wherein the dialysis system is capable of moving fluid bi-directionally in the variable-volume dialysate flow path.

32. The dialysis system of claim 24, wherein the first outlet stream and the second outlet stream have substantially the same concentration of at least one component of the fluid.

33. The dialysis system of claim 24, wherein the first regeneration module operates at a total capacity of the regenerative substance.

34. The dialysis system of claim 24, wherein the regenerative substance comprises at least one of urease, alumina, zirconium phosphate, zirconium oxide, and activated carbon.

35. The dialysis system of claim 24, further comprising:
a third regeneration module containing the first chosen regenerative substance; and
a second mixing chamber, wherein a third outlet stream of the dialysate exits the second mixing chamber and flows through the first mixing chamber, and a fourth outlet stream of the dialysate exits the second mixing chamber and flows through the third regeneration module.

36. The dialysis system of claim 24, further comprising:
an extracorporeal circuit to convey blood from a subject through the dialyzer and back to the subject; and
a replacement fluid circuit to convey a portion of the second outlet stream downstream of the second regeneration module to the extracorporeal circuit downstream of the dialyzer, wherein the dialyzer also facilitates removal of a filtrate from the blood.

37. The dialysis system of claim 36, further comprising a dialysate flow path that allows fluid communication between the dialyzer, the first and second regeneration modules and the first mixing chamber, wherein the dialyzer, the dialysate flow path the first and second regeneration modules and the first mixing chamber have a substantially fixed volume.

38. A filtration system, comprising:
a filter that facilitates removal of a filtrate from blood;
a first regeneration module containing a first chosen regenerative substance;
a second regeneration module containing the first chosen regenerative substance; and
a first mixing chamber, wherein a first outlet stream of the filtrate sequentially exits the first mixing chamber, flows through the first regeneration module in fluid communication with the regenerative substance and returns to the first mixing chamber, and a second outlet stream of the filtrate sequentially exits the first mixing chamber, flows through the second regeneration module in fluid communication with the regenerative substance and flows through the dialyzer.

39. A method of regenerating a fluid, comprising the steps of:
conveying a first outlet stream of the fluid from a first mixing chamber to a first regeneration module containing a first chosen regenerative substance;
removing a waste species from the first outlet stream in fluid communication with the regenerative substance;
returning the first outlet stream to the first mixing chamber;
mixing a first inlet stream of the fluid entering the first mixing chamber with the first outlet stream returned to the first mixing chamber;
conveying a second outlet stream of the fluid from the first mixing chamber to a second regeneration module containing the first chosen regenerative substance; and
removing the waste species from the second outlet stream in fluid communication with the regenerative substance.

40. The method of claim 39, wherein the step of mixing further comprises employing a static mixer element in the mixing chamber.

41. The method of claim 40, wherein the step of mixing further comprises employing a semi-permeable membrane that separates the first inlet stream from the second inlet stream in the first mixing chamber, and a solute diffuses from the first inlet stream to the second inlet stream.

42. The method of claim 40, wherein the step of mixing results in the first outlet stream and the second outlet stream having substantially the same concentration of at least one component of the fluid.

43. The method of claim 40, further comprising operating the first regeneration module at a total capacity of the regenerative substance.

44. The method of claim 40, further comprising:
conveying the second outlet stream from the second regeneration module through a dialyzer; and
conveying the first inlet stream from the dialyzer to the first mixing chamber, wherein the fluid comprises a dialysate solution.

45. The method of claim 40, further comprising:
conveying the second outlet stream from the second regeneration module to a filter;
removing a filtrate from blood through the filter; and
conveying the first inlet stream from the filter to the first mixing chamber, wherein the fluid comprises a filtrate solution.

46. The method of claim 40, further comprising:
wherein the regenerative substance comprises at least one of urease, alumina, zirconium phosphate, zirconium oxide, or activated carbon.

47. The method of claim 40, further comprising:
conveying the second outlet stream from the second regeneration module to a second mixing chamber;
mixing a third inlet stream of the fluid entering the second mixing chamber with the second outlet stream;
conveying a third outlet stream of the fluid from the second mixing chamber to the first mixing chamber;
conveying a fourth outlet stream of the fluid from the second mixing chamber to a third regeneration module containing the first chosen regenerative substance; and
removing the waste species from the fourth outlet stream in fluid communication with the regenerative substance; wherein the first inlet stream consists of the third outlet stream.

48. The regeneration system of claim 1, further comprising a microbial filter positioned downstream of the first mixing chamber along a fluid flow.

49. The regeneration system of claim 48, further comprising a replacement fluid pump upstream of the microbial filter along the fluid flow.

50. The regeneration system of claim 1, further comprising a first pump positioned upstream of the first regeneration module and a second pump positioned upstream of the second regeneration module.

51. The regeneration system of claim 1, wherein at least one of the first and second regeneration modules includes first and second compartments, the first and second compartments being separated with a barrier oriented in a direction substantially parallel to a fluid flow.

52. The regeneration system of claim 51, wherein the first and second compartments are different in composition.

\* \* \* \* \*